United States Patent
Dressman et al.

(10) Patent No.: US 9,056,844 B2
(45) Date of Patent: Jun. 16, 2015

(54) 4-SUBSTITUTED-3-BENZYLOXY-BICYCLO [3.1.0]HEXANE COMPOUNDS AS MGLUR 2/3 ANTAGONISTS

(75) Inventors: Bruce Anthony Dressman, Indianapolis, IN (US); Mark Donald Chappell, Indianapolis, IN (US); Adam Michael Fivush, Fishers, IN (US); Charles Howard Mitch, Columbus, IN (US); Paul Leslie Ornstein, Carmel, IN (US); Eric George Tromiczak, Indianapolis, IN (US); Tatiana Natali Vetman, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/883,788

(22) PCT Filed: Nov. 15, 2011

(86) PCT No.: PCT/US2011/060686
§ 371 (c)(1),
(2), (4) Date: May 7, 2013

(87) PCT Pub. No.: WO2012/068041
PCT Pub. Date: May 24, 2012

(65) Prior Publication Data
US 2013/0237573 A1 Sep. 12, 2013

Related U.S. Application Data

(60) Provisional application No. 61/415,113, filed on Nov. 18, 2010.

(51) Int. Cl.
| | |
|---|---|
| *A61K 31/4196* | (2006.01) |
| *A61K 31/426* | (2006.01) |
| *A61K 31/216* | (2006.01) |
| *A61K 31/4164* | (2006.01) |
| *C07D 277/36* | (2006.01) |
| *A61K 31/138* | (2006.01) |
| *A61K 45/06* | (2006.01) |
| *C07C 229/50* | (2006.01) |
| *C07C 233/52* | (2006.01) |
| *C07C 235/14* | (2006.01) |
| *C07C 271/24* | (2006.01) |
| *A61K 31/135* | (2006.01) |
| *A61K 31/196* | (2006.01) |
| *A61K 31/265* | (2006.01) |
| *A61K 31/27* | (2006.01) |
| *C07C 62/34* | (2006.01) |
| *C07C 69/757* | (2006.01) |

(Continued)

(52) U.S. Cl.
CPC .......... *C07D 277/36* (2013.01); *A61K 31/138* (2013.01); *A61K 45/06* (2013.01); *C07C 229/50* (2013.01); *C07C 233/52* (2013.01); *C07C 235/14* (2013.01); *C07C 271/24* (2013.01); *C07C 2101/02* (2013.01); *C07C 2102/18* (2013.01); *A61K 31/135* (2013.01); *A61K 31/196* (2013.01); *A61K 31/216* (2013.01); *A61K 31/265* (2013.01); *A61K 31/27* (2013.01); *A61K 31/4164* (2013.01); *A61K 31/4196* (2013.01); *A61K 31/426* (2013.01); *C07C 62/34* (2013.01); *C07C 69/757* (2013.01); *C07C 69/96* (2013.01); *C07D 235/00* (2013.01); *C07D 249/12* (2013.01)

(58) Field of Classification Search
CPC ............ A61K 31/216; A61K 31/4164; A61K 31/4196; A61K 31/426
USPC .................................................. 514/369, 365
See application file for complete search history.

(56) References Cited

U.S. PATENT DOCUMENTS

| | | | |
|---|---|---|---|
| 5,916,920 A | 6/1999 | Yasuhara et al. | |
| 6,107,342 A | 8/2000 | Adam et al. | |

(Continued)

FOREIGN PATENT DOCUMENTS

| | | |
|---|---|---|
| EP | 0774455 A1 | 5/1997 |
| EP | 1897550 A2 | 12/2008 |

(Continued)

OTHER PUBLICATIONS

Yasuhara et al. "Synthesis, in vitro pharmacology, and structure-activity relationships of 2-aminobicyclo [3.1.0jhexane-2,6-dicarboxylic acid derivatives as mGluR2 antagonists" Bioorganic & Medicinal Chemistry 14 (2006) 3405-3420.

(Continued)

*Primary Examiner* — Jeffrey S Lundgren
*Assistant Examiner* — Chris Simmons
(74) *Attorney, Agent, or Firm* — R. Craig Tucker

(57) ABSTRACT

A mGlu2/3 receptor antagonist of the formula:

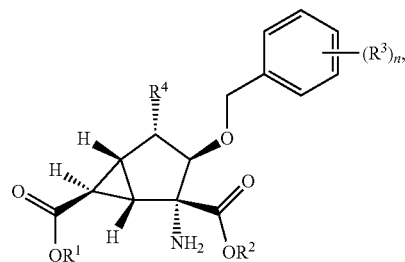

its uses, and methods for its preparation are described.

12 Claims, No Drawings

(51) Int. Cl.
*C07C 69/96* (2006.01)
*C07D 235/00* (2006.01)
*C07D 249/12* (2006.01)

(56) References Cited

U.S. PATENT DOCUMENTS

| | | | |
|---|---|---|---|
| 7,157,594 B2 | 1/2007 | Nakazato et al. | |
| 7,381,746 B2 | 6/2008 | Yasuhara et al. | |
| 2005/0222231 A1* | 10/2005 | Moher et al. | 514/381 |
| 2006/0142388 A1 | 6/2006 | Yasuhara et al. | |
| 2007/0021394 A1* | 1/2007 | Yasuhara et al. | 514/151 |

FOREIGN PATENT DOCUMENTS

| | | |
|---|---|---|
| JP | 339199 | 12/2004 |
| JP | 193507 | 7/2006 |
| WO | 99/47490 A1 | 9/1999 |
| WO | 00/04010 A1 | 1/2000 |
| WO | 2005/000789 A1 | 1/2005 |

OTHER PUBLICATIONS

Yasuhara et al. "Prodrugs of 3-(3,4-dichlorobenzyloxy)-2-aiiiino-6-fluorobicyclo[3.1.01hexane-2,6-dicarboxylic acid (MGS0039): A potent and orally active group II mGluR antagonist with antidepressant-like potential" Bioorganic & Medidnal Chemistry 14 (2006) 4193-4207.

Dominguez, et al., Asymmetric synthesis of (+)-2-aminobicyclo[3.1.0]hexane-2,6-dicarboxyUc acid (LY354740), Tetrahedron: Asymmetry, vol. 8, No. 4: 511-514, (1997).

Li, et al., Metabotropic Glutamate 5 Receptor Antagonism Is Associated with Antidepressant-Like Effects in Mice, The J. of Pharmacology and Experimental Therapeutics, vol. 319: 1, 254-259 (2006).

Yasuhara, et al., Metabotropic Glutamate Receptors: Potential Drug Targets for Psychiatric Disorders, The Open Med. Chemistry Journal, 4: 20-36 (2010).

Kuo, et al., Synthesis of LY455169-2H2, A Model Study for the Trituium Labeling of LY459477. 2. Synthesis of LY459477-[3H2], Synthesis and Applications of Isotopically Labelled Compounds, vol. 8 (2004).

Sakagami, et al., Synthesis, in vitro pharmacology, and pharmacokinetic profiles of 2-[1-amino-1-carboxy-2-(9H-xanthen-9-yl)ethyl]-1-fluoro-cyclopropanecarboxylic acid and its 6-heptyl ester, a potent mGluR2 antagonist Bioorganic & Medicinal Chemistry 16: 4359-4366 (2008).

Nakazato, et al., Synthesis SARs, and Pharmacological Characterization of 2-Amino-3 or 6-fluorobicyclo[3.1.0] hexane-2,6-dicarboxylic Acid Derivatives as Potent, Selective, and Orally Active Group II Metabotropic Glutamate Receptor Agonists, J. Med. Chem., 43: 4893-4909 (2000).

Dominguez, et al., Enantiospecific synthesis of (1S,2S,5R,6S)-2-Aminobicyclo[3.1.0]hexane-2,6-dicarboxylic acid by a modified Corey-Link reaction[1], Tetrahedron Letters 39: 9305-9308 (1998).

Witkin, et al., Antagonism of Metabotropic Glutamate Group II Receptors in the Potential Treatment of Neurological and Neuropsychiatric Disorders, Drug Development Research 67: 757-769 (2006).

* cited by examiner

4-SUBSTITUTED-3-BENZYLOXY-BICYCLO [3.1.0]HEXANE COMPOUNDS AS MGLUR 2/3 ANTAGONISTS

This U.S. national stage application of International Application PCT/US2011/060686, filed Nov. 15, 2011, claims priority to U.S. provisional application Ser. No. 61/415,113, filed Nov. 18, 2010.

Glutamate is the major excitatory neurotransmitter in the brain and is involved in a wide variety of physiological processes mediated through no less than 11 distinct receptors, each with its own pharmacology. Metabotropic Glutamate Receptor subtypes 2 and 3 (known as mGlu2 and mGlu3) are often grouped together as Group II mGlu receptors based on their sequence homology, similar second messenger coupling, and similar pharmacological characteristics. Antagonists of mGlu2/3 receptors have exhibited significant pharmacological effects in animal models for depressive disorders and disorders of excessive sleepiness. As such, mGlu2/3 antagonists are deemed to be useful in the treatment of depressive disorders such as major depressive disorder (MDD), unipolar depression, dysthymia, and/or cyclothymia, and/or useful in the treatment of disorders of excessive sleepiness, such as excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS).

U.S. Pat. No. 5,916,920 describes certain 3-monosubstituted bicyclo[3.1.0]hexane compounds as metabotropic glutamate receptor modulators useful for treating a variety of disorders including as antidepressant agents. U.S. Pat. No. 7,157,594 describes various 3-monosubstituted bicyclo [3.1.0]hexane compounds as Group II mGlu receptor antagonists for use in treating various disorders including depressive symptoms. US 2007/0021394 A1 describes various 3-monosubstituted bicyclo[3.1.0]hexane compounds as Group II mGlu receptor antagonists and prodrugs thereof for use in treating various disorders including depression.

The present invention provides a family of 4-substituted-3-phenylsulfanylmethyl-bicyclo[3.1.0]hexane compounds with high antagonist potency for the mGlu2 and mGlu3 receptors. The compounds of the present invention are also selective for the mGlu2 and mGlu3 receptors, particular as against other mGlu receptors. Certain compounds have also demonstrated through animal models that the compounds of the present invention may be useful for the treatment of depressive disorders (which may include major depressive disorder (MDD), unipolar depression, dysthymia, and/or cyclothymia) and disorders of excessive sleepiness (which may include excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS)). The antidepressant-like and wake-promoting effects of this mechanism also predict impact on symptoms of depressive disorders such as fatigue that are otherwise difficult to treat with existing antidepressants.

The present invention provides compounds of Formula I:

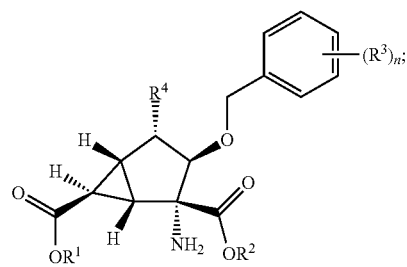

where $R^1$ and $R^2$ are each independently hydrogen, $C_1$-$C_3$ alkoxycarbonyloxymethyl, $C_1$-$C_3$ alkylcarbonyloxymethyl, or $C_{3-6}$ cycloalkylcarbonyloxymethyl;

$R^3$ is independently at each occurance methyl, fluoro, or chloro;

$R^4$ is hydroxyl, methylcarbonylamino, hydroxymethylcarbonylamino, methoxycarbonylamino, imidazol-2-ylsulfanyl, thiazol-2-ylsulfanyl, 1,2,4-triazol-3-ylsulfanyl, 1-methyl-1, 2,4-triazol-3-ylsulfanyl, or 1-methyl-1,2,4-triazol-5-ylsulfanyl; and n is 1 of 2;

or a pharmaceutically acceptable salt thereof.

It is a feature of the present invention that compounds of Formula I wherein $R^1$ and $R^2$ are both hydrogen (the di-acid compounds) are the therapeutically active compounds in vivo, whereas compounds where $R^1$ or $R^2$ or both are other than hydrogen are prodrugs of their therapeutically active di-acid analogs. The compounds where $R^1$ or $R^2$ or both are other than hydrogen are hydrolyzed in vivo to provide the therapeutically active di-acid analog. The prodrug compounds when administered orally, particularly di-ester prodrugs, provide improved bioavailability of the di-acid metabolite compared to oral administration of the di-acid compounds ($R^1$ and $R^2$ both hydrogen), but the di-acid compounds provide better activities when administered intravenously, intramuscularly or subcutaneously.

In another aspect of the invention there is provided a pharmaceutical composition comprising a compound of Formula I or a pharmaceutically acceptable salt thereof, in combination with at least one pharmaceutically acceptable carrier, diluent, or excipient. Furthermore, this aspect of the invention provides a pharmaceutical composition adapted for the treatment of depressive disorders, as for example major depressive disorder, unipolar depression, dysthymia, and/or cyclothymia, comprising a compound of Formula I or a pharmaceutically acceptable salt thereof, in combination with one or more pharmaceutically acceptable excipients, carriers, or diluents thereof.

A further embodiment of this aspect of the invention provides a pharmaceutical composition comprising a compound according to Formula I, or pharmaceutically acceptable salt thereof, in combination with at least one pharmaceutically acceptable carrier, excipient or diluents, and optionally other therapeutic ingredients. In a yet further embodiment of this aspect of the invention, the pharmaceutical composition further comprises a second therapeutic agent which is a drug useful in the treatment of depressive disorders, as for example a serotonin reuptake inhibitor, as for example fluoxetine and/or citalopram.

In yet another embodiment of this aspect of the invention there is provided a pharmaceutical composition adapted for the treatment of disorders of excessive sleepiness, as for example, excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and/or excessive sleepiness associated with non-restorative sleep (NRS), comprising a compound of Formula I or a pharmaceutically acceptable salt thereof, in combination with one or more pharmaceutically acceptable excipients, carriers, or diluents thereof.

The present invention also provides a method of treating depressive disorders, as for example major depressive disorder (MDD), unipolar depression, dysthymia, and/or cyclothymia, in a mammal comprising administering to a mammal in need of such treatment an effective amount of a compound of Formula I or a pharmaceutically acceptable salt thereof. In another embodiment of this aspect of the invention, the method further comprises administering in simultaneous, separate or sequential combination, a second therapeutic agent which is a drug useful in the treatment of depressive disorders, as for example a serotonin reuptake inhibitor, as for example fluoxetine and/or citalopram.

Other embodiments of the invention provide methods of treating disorders of excessive sleepiness comprising administering to a mammal in need of such treatment an effective amount of a compound of Formula I, or a pharmaceutically acceptable salt thereof. In other embodiments of this aspect of the invention, the excessive sleepiness is due to any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

In one particular embodiment of these methods of treatment, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of depressive disorders. In further embodiments, the depressive disorder is any one of major depressive disorder (MDD), unipolar depression, dysthymia, and/or cyclothymia. In another embodiment of this aspect of the invention, the invention provides a compound according to Formula I, or a pharmaceutically acceptable salt thereof, for use in simultaneous, separate or sequential combination with a serotonin reuptake inhibitor, as for example fluoxetine and/or citalopram, in the treatment of depressive disorders.

Further, this aspect of the invention includes a compound of Formula I, or a pharmaceutically acceptable salt thereof, for use in the treatment of disorders of excessive sleepiness. In particular embodiments of this aspect of the invention, the excessive sleepiness is due to any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

One particular embodiment of this aspect of the inventions, the uses are in mammals, particular humans.

Another aspect of this invention provides the use of a compound of Formula I, or a pharmaceutically acceptable salt thereof, in the manufacture of a medicament for the treatment of depressive disorders, as for example major depressive disorder (MDD), unipolar depression, dysthymia, and/or cyclothymia. Another embodiment of this aspect of the invention provides the use of a compound of Formula I, or a pharmaceutically acceptable salt thereof, and a second therapeutic agent useful in the treatment of depressive disorders, as for example a serotonin reuptake inhibitor, as for example fluoxetine and/or citalopram, in the manufacture of a medicament for the treatment of depressive disorders. Another embodiment of the invention provides the use of a compound of Formula I, or a pharmaceutically acceptable salt thereof, in the manufacture of a medicament for the treatment of disorders of excessive sleepiness. In particular embodiments of this aspect of the invention, the medicament is for the treatment of any one or more of the following: excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance or excessive sleepiness associated with non-restorative sleep (NRS).

Compounds of this invention have basic and acidic moieties, and accordingly react with a number of organic and inorganic acids and bases to form pharmaceutically acceptable salts. Pharmaceutically acceptable salts of each of the compounds of the present invention are contemplated within the scope of the present application. The term "pharmaceutically acceptable salt" as used herein, refers to any salt of a compound of the invention that is substantially non-toxic to living organisms. Such salts include those listed in *Journal of Pharmaceutical Science*, 66, 2-19 (1977), which are known to the skilled artisan.

Preferred classes of compounds of the present invention are compounds wherein:

1) $R^1$ and $R^2$ are both hydrogen;
2) $R^1$ or $R^2$ or both are other than hydrogen;
3) $R^1$ and $R^2$ are both other than hydrogen;
4) $R^1$ and $R^2$ are the same and are other than hydrogen;
5) $R^1$ and $R^2$ are each isopropoxycarbonyloxymethyl;
6) n is 2;
7) n is 2, both $R^3$ groups are chloro, and the chloro groups are at the phenyl 3- and 4-positions;
8) $R^4$ is hydroxyl.

It will be understood that further preferred compounds are those combining the above preferred selections for a given substituents with preferred selections of other substituents. Examples of such combinations include, but are not limited to the following preferred classes of compounds:

9) preferred compounds of any one of paragraphs 1-5 (preferred selections for $R^1$ and $R^2$) wherein n is 2, both $R^3$ groups are chloro, and the chloro groups are at the phenyl 3- and 4-positions (paragraph 7);
10) preferred compounds of any one of paragraphs 1-5 (preferred selections for $R^1$ and $R^2$) wherein $R^4$ is hydroxyl (paragraph 8);
11) preferred compounds of any one of paragraphs 1-5 (preferred selections for $R^1$ and $R^2$) wherein n is 2, both $R^3$ groups are chloro, and the chloro groups are at the phenyl 3- and 4-positions (paragraph 7), and where $R^4$ is hydroxyl (paragraph 8).

Specific preferred compounds of the invention are those described in the examples, including their free bases and pharmaceutically acceptable salts thereof.

Certain preferred compounds are:
(1S,2R,3 S,4S,5R,6R)-2-amino-3-[(3,4-dichlorobenzyl)oxy]-4-hydroxybicyclo[3.1.0]hexane-2,6-dicarboxylic acid or a pharmaceutically acceptable salt thereof; and
bis(isopropoxycarbonyloxymethyl)(1R,2S,3S,4R,5S,6R)-4-amino-3-[(3,4-dichlorophenyl)methoxy]-2-hydroxy-bicyclo[3.1.0]hexane-4,6-dicarboxylate or a pharmaceutically acceptable salt thereof (i.e. the compounds of Examples 1, 10 and 15, and alternative pharmaceutically acceptable salts thereof).

Abbreviations used herein are defined as follows:
"BSA" means bovine serum albumin.
"DCG IV" means (2S,2'R,3'R)-2-(2',3'-dicarboxycyclopropyl)glycine.
"DMEM means Dulbecco's Minimum Eagle's Medium.
"DMSO" means dimethyl sulfoxide.
"DPBS" means Dulbecco's Phosphate Buffered Saline.
"EDTA" means ethylene diamine tetraacetic acid.
"GTP" means guanosine triphosphate.
"HBSS" means Hank's Buffered Salt Solution.
"HEPES" means 4-(2-hydroxyethyl)-1-piperazineethanesulfonic acid.
"HPLC" means high-pressure liquid chromatography.
"IBMX" means 3-isobutyl-1-methylxanthine "IC$_{50}$" means the concentration at which 50% of the maximum inhibition is achieved.
"i.v." means intravenous or intravenously.
"i.p." means intraperitoneal.
"L-AP-4" means L-(+)-2-amino-4-phosphonobutyric acid.
"LC/MS" means liquid chromatography followed by mass spectroscopy.
"mFST" means mouse forced swim test; an animal model for antidepressant activity.
"MS" means mass spectroscopy.
"MS (ES+)" means mass spectroscopy using electrospray ionization.
"NMR" means nuclear magnetic resonance.
"p.o." means per os, by mouth.
"tBu" means a tertiary-butyl moiety.

General Chemistry

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties, as is well appreciated by the skilled chemist. All substituents, unless otherwise indicated, are as previously defined, and all reagents are well known and appreciated in the art.

Prodrug compounds 1 may be prepared as illustrated in Scheme I where $R^1$, $R^2$, $R^3$, $R^4$, and n are as previously defined. $R^1$ and $R^2$ are not both hydrogen in compound 1.

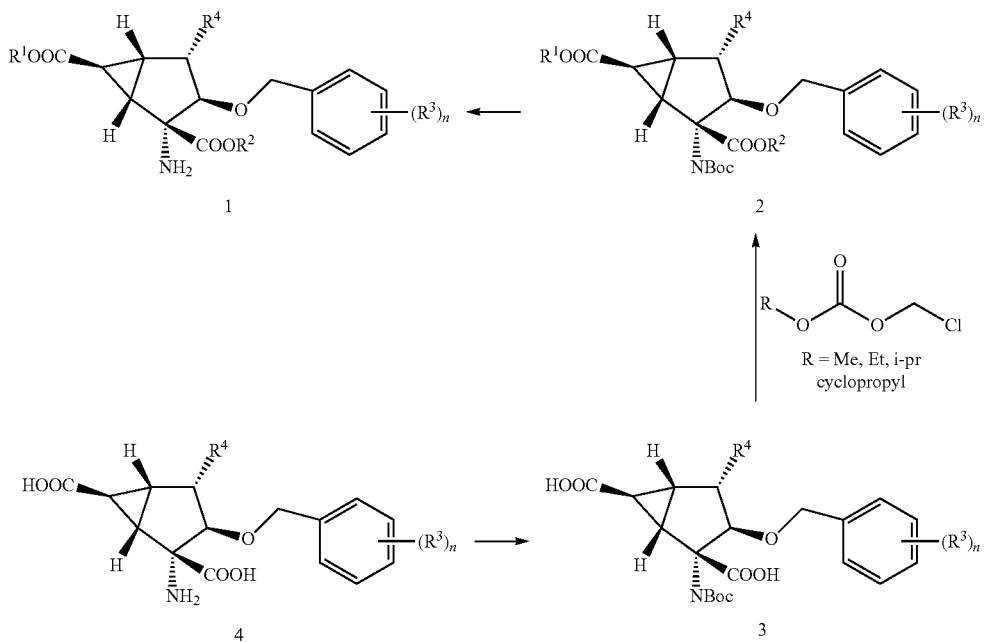

Scheme I

The compounds 1 can be made by chemistry illustrated in Scheme I. Compound 4 is reacted with an amino protecting reagent such as di-tert-butyldicarbonate under conditions well known to the skilled artisan to provide the compound 3. When the $R^1$ and $R^2$ groups are identical in the compound 2, the compound 3 is reacted with sufficient amount of proper chloro- or iodomethyl alkyl carbonate and appropriate reagents such as sodium iodide and cesium carbonate in a suitable solvent such as dimethylformamide to give the desired di-ester compound 2 where $R^1$ and $R^2$ are the same. When $R^1$ and $R^2$ are different in compound 2, by controlling the amount of first chloromethyl alkyl carbonate to about one equivalent, the carboxylic acid on the five-membered ring can be converted to a $R^2$ mono ester first. The $R^2$ mono ester compound can further react with one equivalent of different chloromethyl alkyl carbonate. The free carboxylic acid group on the three-membered ring can then be converted to a $R^1$ ester to provide the desired di-ester with different $R^1$ and $R^2$. To make a $R^2$ mono ester on the five membered ring of the compound 2, the compound 3 is reacted with about one equivalent of proper chloromethyl alkyl carbonate and appropriate reagents such as sodium iodide and cesium carbonate in a suitable solvent such as dimethylformamide to give the desired $R^2$ mono ester compound 2, in which $R^1$ is hydrogen. To make a $R^1$ mono ester on the three-membered ring, the carboxylic acid group on the five-membered ring should be protected first since it is more reactive. More specifically, the carboxylic acid group on the five-membered ring in compound 3 can react with alpha-chloro-4-methoxytoluene, sodium iodide and sodium bicarbonate in a suitable solvent such as dimethylformamide to provide a 4-methoxylbenzyl mono ester. The free carboxylic acid group on the three-membered ring of the protected 4-methoxylbenzyl mono ester compound is then reacted with a proper chloromethyl alkyl carbonate to afford a desired $R^1$ ester on the three-membered ring. The di-ester is treated with a proper acid such as trifluoroacetic acid to deprotect both 4-methoxylbenzyl and N-tert-butoxycarbonyl group to afford the desired $R^1$ mono ester compound 1. The compound 2, including $R^2$ mono ester and di-ester with same or different $R^1$ and $R^2$, is then de-protected with a proper acid such as hydrochloric acid in dioxane to give the desired compound 1 or a pharmaceutically acceptable salt.

Scheme II

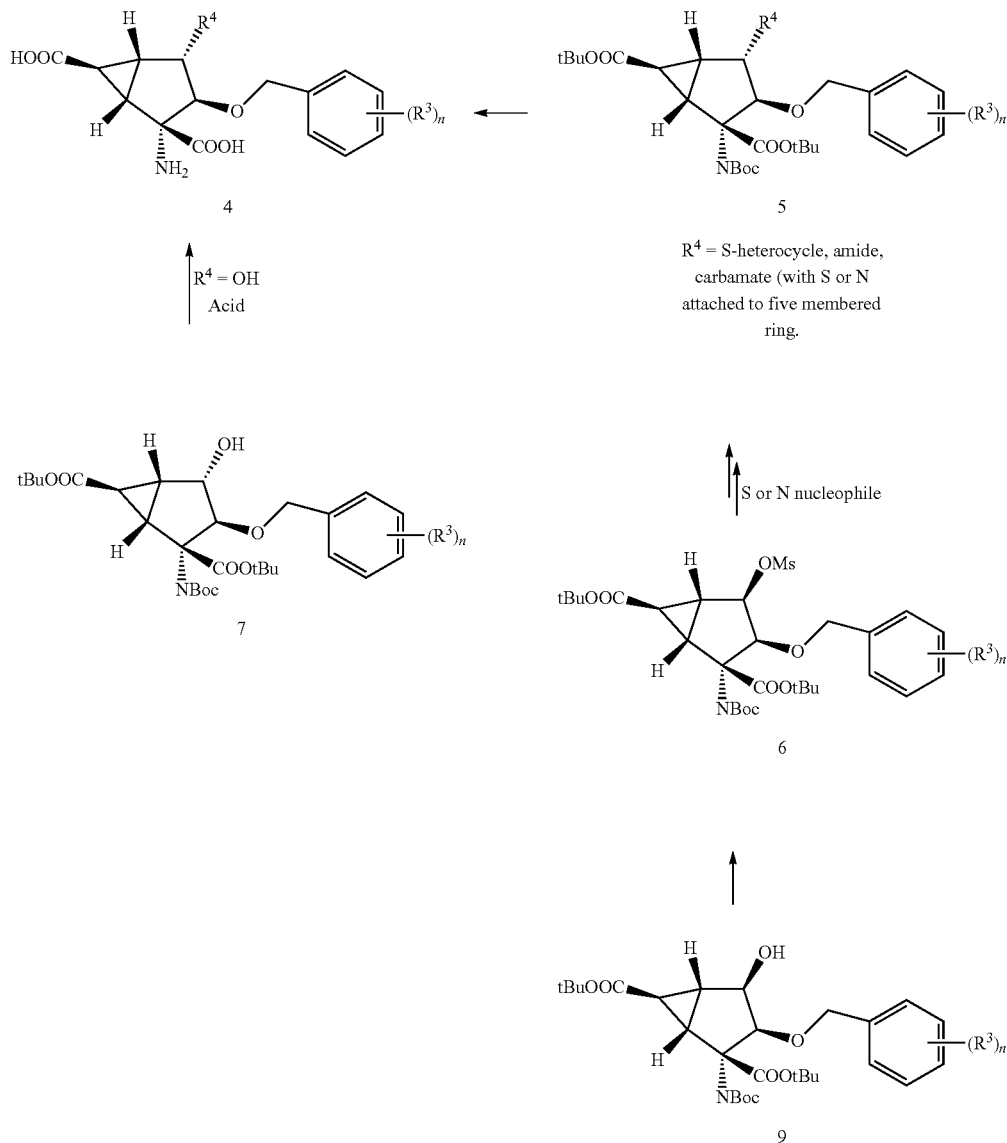

Active parent compound 4 may be prepared as illustrated in Scheme II.

Compound 9 is reacted with methanesulfonyl chloride and a proper base such as triethylamine in a suitable solvent such as tetrahydrofuran to give the mesylate compound 6. Compound 6 can react with thiol heterocycles such as 1H-1,2,4-triazole-3-thiol and a suitable base such as potassium carbonate in a solvent such as dimethylformamide to give the desired compound 5, in which $R^4$ is a desired thio linked heterocycle. Compound 6 can also react with sodium azide to give an azide intermediate, which is then reduced with trimethylphosphine in tetrahydrofuran and water to provide an amine. The resulted amine can further form a desired amide or carbamate with methods well known to skilled artisans to give compound 5, in which $R^4$ is a desired amide or carbamate group. The compound 5 is then de-protected with proper acid such as hydrochloric acid or acetic acid to give the compound 4. When $R^4$ is hydroxyl group in compound 4, the desired active parent compound 4 can be made directly from compound 7 by removing all protecting groups with a proper acid such as HCl in a suitable solvent such as dioxane.

The two key intermediates 7 and 9 can be prepared as illustrated in Scheme III.

Compound 14 (See WO03/104217/A2 for synthesis details) is reduced to compound 13 with proper reducing reagent such as lithium tri(sec-butyl)borohydride in a proper solvent such as tetrahydrofuran. Compound 13 is reacted with methanesulfonyl chloride and a base such as triethyamine in a proper solvent such as tetrahydrofuran to give mesylate compound 12, which is further reacted with trabutylammonium fluoride or potassium tert-butoxide in tetrahydrofuran to give compound 11. Compound 11 is reacted with $OsO_4$, N-methylmorpholine-N-oxide in acetone and water to give a diol compound 10. Compound 10 is then reacted with properly substituted benzyl halide such as 3,4-dichlorobenzyl bromide, using tetra-n-butylammonium iodide and silver oxide in suitable solvent such as dimethylformamide to afford the compound 9. Under Mitsunobu reaction condition, compound 9 is reacted with 4-nitrobenzoic acid, triphenylphosphine, and diisopropyl azodicarboxylate in a proper solvent such as tetrahydrofuran to yield the compound 8. Compound

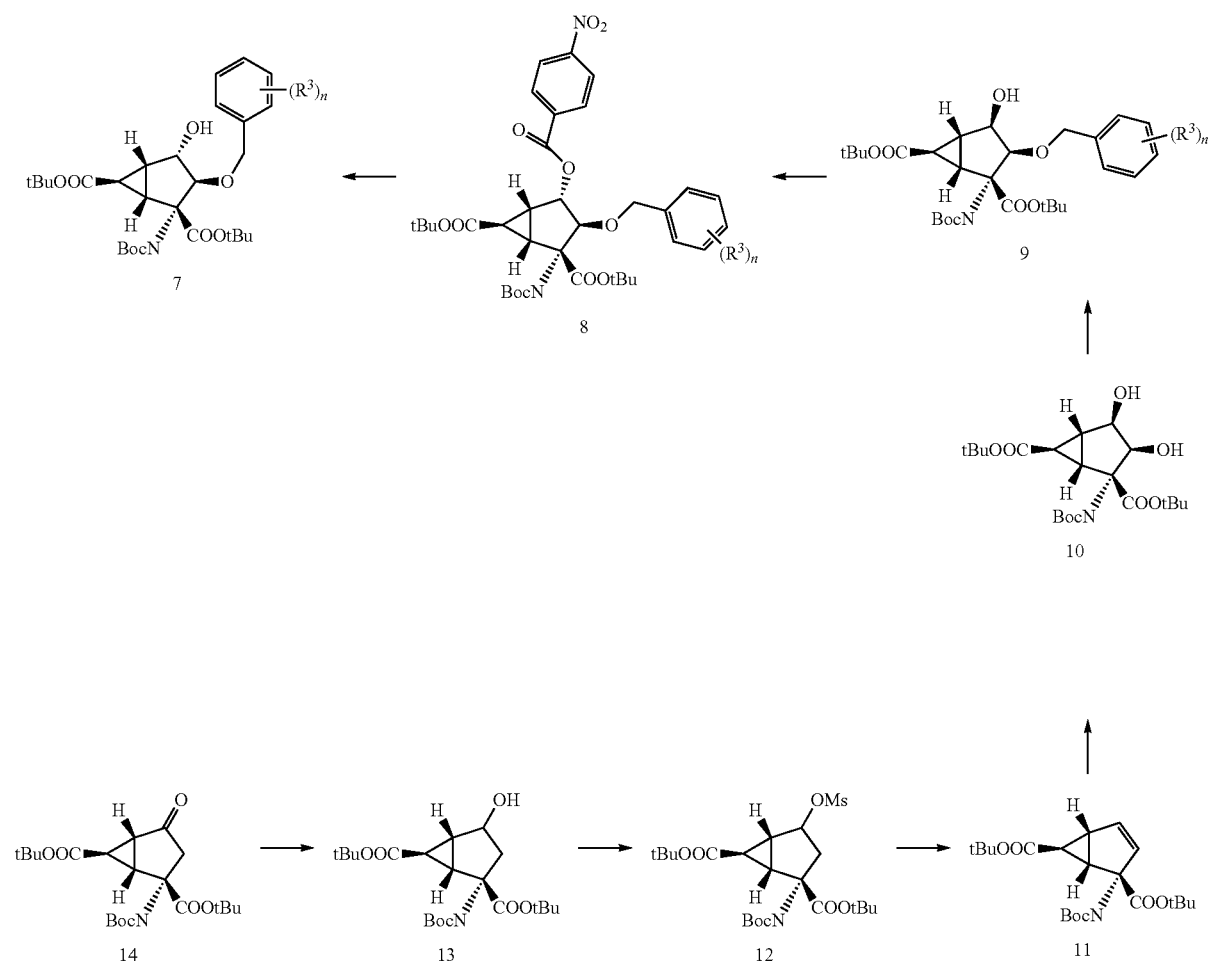

Scheme III 8 is then reacted with potassium carbonate in a suitable solvent such as methanol to provide the compound 7.

Preparation 1: Di-tert-butyl (1S,2S,4S,5R,6R)-2-[(tert-butoxycarbonyl)amino]-4-hydroxy-bicyclo[3.1.0]hexane-2,6-dicarboxylate

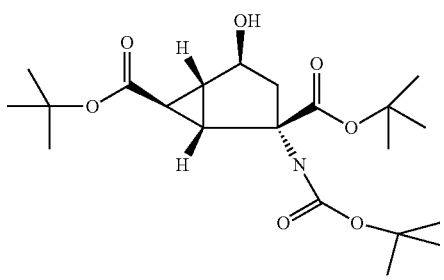 [SMILES: CC(C)(C)OC(=O)N[C@@]1(C(=O)OC(C)(C)C)C[C@H](O)[C@H]2[C@H](C(=O)OC(C)(C)C)[C@H]21]

Add 1M lithium tri(sec-butyl)borohydride in tetrahydrofuran (42.27 mL, 42.27 mmol) dropwise to di-tert-butyl (1S,2S,5R,6R)-2-[(tert-butoxycarbonyl)amino]-4-oxobicyclo[3.1.0]hexane-2,6-dicarboxylate (7.10 g, 17.25 mmol, see WO03/104217/A2 for synthesis details) in tetrahydrofuran (431.35 mL) at 0° C. and stir. After 90 minutes, carefully add 1M aqueous sodium bicarbonate (60.07 mL, 62.11 mmol) followed by hydrogen peroxide (30% wt, 2.64 mL, 86.27 mmol) at 0° C. The reaction is warmed to room temperature. After 40 minutes, the reaction is extracted with ethyl acetate, washed with 10% aqueous citric acid followed by brine, dried over sodium sulfate, filtered, and concentrated under reduced pressure to give a residue. The residue is purified by flash chromatography eluting with 5-50% ethyl acetate in hexanes to give the title compound (6.70 g, 16.20 mmol, 94%).

Preparation 2: Di-tert-butyl (1S,2S,4S,5R,6R)-2-[(tert-butoxycarbonyl)amino]-4-[(methylsulfonyl)oxy]bicyclo[3.1.0]hexane-2,6-dicarboxylate

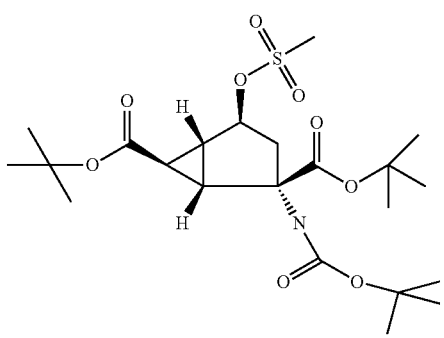 [SMILES: CC(C)(C)OC(=O)N[C@@]1(C(=O)OC(C)(C)C)C[C@H](OS(C)(=O)=O)[C@H]2[C@H](C(=O)OC(C)(C)C)[C@H]21]

Methanesulfonyl chloride (224.61 µL, 2.90 mmol) is added to di-tert-butyl (1S,2S,4S,5R,6R)-2-[(tert-butoxycarbonyl)amino]-4-hydroxy-bicyclo[3.1.0]hexane-2,6-dicarboxylate (400 mg, 967 µmoles) and triethylamine (472 µL, 3.39 mmol) in tetrahydrofuran (4.84 mL) at 0° C. and stirred. Cooling bath is removed and the reaction is allowed to warm to room temperature and stirred overnight. Dilute with water and saturated aqueous sodium bicarbonate then extract with ethyl acetate. The combined organics are washed with brine, dried over sodium sulfate, filtered, and concentrated to under reduced pressure to give the title compound (600 mg, 1.22 mmol, 100%).

Preparation 3: Di-tert-butyl (1S,2S,5R,6S)-2-[(tert-butoxycarbonyl)amino]bicyclo[3.1.0]hex-3-ene-2,6-dicarboxylate

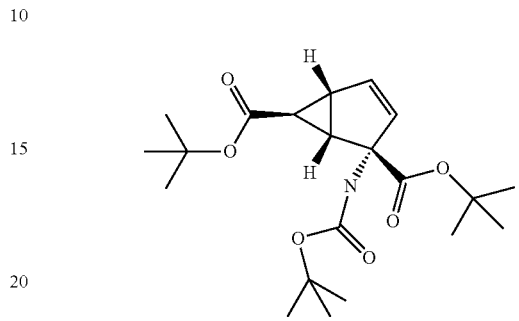

Add 1M tetrabutylammonium fluoride in tetrahydrofuran (3.84 mL, 3.84 mmol) to di-tert-butyl (1S,2S,4S,5R,6R)-2-[(tert-butoxycarbonyl)amino]-4-[(methylsulfonyl)oxy]bicyclo[3.1.0]hexane-2,6-dicarboxylate (600.00 mg, 1.22 mmol) in tetrahydrofuran (2.03 mL) and heat at reflux for 3 hours. The reaction is then cooled to room temperature, diluted with water, and extracted with ethyl acetate, washed with brine, dried over sodium sulfate, filtered, and concentrated under reduced pressure to give a residue. The residue is purified by flash chromatography eluting with 5-75% ethyl acetate in hexanes to give the title compound (0.23 g, 0.58 mmol, 48%).

Preparation 4: Di-tert-butyl (1S,2R,3S,4R,5R,6R)-2-[(tert-butoxycarbonyl)amino]-3,4-dihydroxybicyclo[3.1.0]hexane-2,6-dicarboxylate

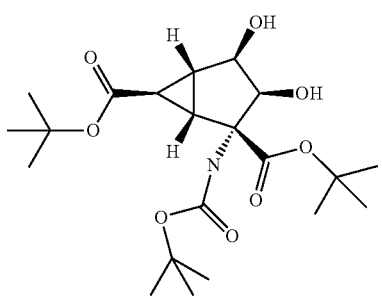 [SMILES: CC(C)(C)OC(=O)N[C@]1(C(=O)OC(C)(C)C)[C@@H]2[C@@H](C(=O)OC(C)(C)C)[C@@H]2[C@@H](O)[C@H]1O]

Add OsO4 (2.5%) in 2-methyl-2-propanol (5.48 g, 0.54 mmol) to N-methylmorpholine-N-oxide (2.43 g, 17.97 mmol), di-tert-butyl (1S,2S,5R,6S)-2-[(tert-butoxycarbonyl)amino]bicyclo[3.1.0]hex-3-ene-2,6-dicarboxylate (3.23 g, 8.17 mmol), acetone (80.66 g, 102.09 mL, 1.39 moles), and water (40.83 mL; 40.83 g, 2.27 moles). Stir at room temperature. After 5 hours, a saturated, aqueous solution of sodium thiosulphate (10 mL) is added to the reaction. Concentrate to half volume under reduced pressure. Dilute the concentrate with water, extract with ethyl acetate (3×50 mL). The combined organic layers are washed with brine, dried over sodium sulfate, filtered, and concentrated under reduced pressure to give a residue. The residue is purified by flash chromatography eluting with 5-50% ethyl acetate in hexanes to give the title compound (2.7 g, 6.3 mmol; 77%)

Preparation 5: Di-tert-butyl (1S,2R,3S,4R,5R,6R)-2-[(tert-butoxycarbonyl)amino]-3-[(3,4-dichlorobenzyl)oxy]-4-hydroxybicyclo[3.1.0]hexane-2,6-dicarboxylate

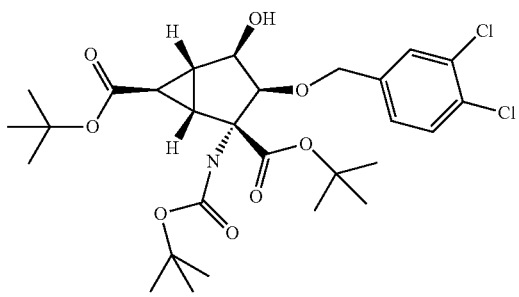 [SMILES: CC(C)(C)OC(=O)N[C@]1(C(=O)OC(C)(C)C)[C@@H]2[C@@H](C(=O)OC(C)(C)C)[C@@H]2[C@@H](O)[C@H]1OCc1ccc(Cl)c(Cl)c1]

Add 3,4-dichlorobenzyl bromide (1.02 mL, 1.02 g, 4.26 mmol) to di-tert-butyl (1S,2R,3S,4R,5R,6R)-2-[(tert-butoxycarbonyl)amino]-3,4-dihydroxybicyclo[3.1.0]hexane-2,6-dicarboxylate (1.22 g, 2.84 mmol), tetra-n-butylammonium iodide (1.07 g, 2.84 mmol) and silver oxide (987.35 mg, 4.26 mmol) in dimethylformamide (17 mL) at room temperature. Stir overnight. Dilute with diethyl ether and hexanes (1:1), filter through celite, and then wash with ether and hexanes (1:1). The filtrate is washed with water, brine, dried over magnesium sulfate, and concentrated under reduced pressure to give a residue. The residue is purified by flash chromatography, eluting with 0-30% ethyl acetate:hexanes to give the title compound (1.7 g, 2.84 mmol, 78%): MS (m/z): 610/612 (M+Na).

Preparation 6: Di-tert-butyl (1S,2R,3S,4S,5R,6R)-2-[(tert-butoxycarbonyl)amino]-3-[(3,4-dichlorobenzyl)oxy]-4-{[(4-nitrophenyl)carbonyl]oxy}bicyclo[3.1.0]hexane-2,6-dicarboxylate

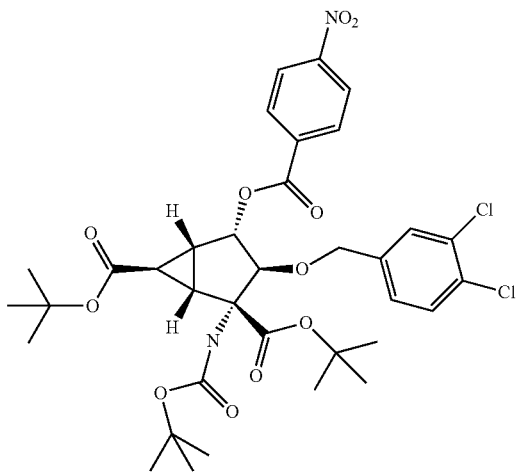 [SMILES: CC(C)(C)OC(=O)N[C@]1(C(=O)OC(C)(C)C)[C@@H]2[C@@H](C(=O)OC(C)(C)C)[C@@H]2[C@H](OC(=O)c2ccc([N+](=O)[O-])cc2)[C@H]1OCc1ccc(Cl)c(Cl)c1]

Triphenylphosphine (12.66 g, 48.26 mmol) and 4-nitrobenzoic acid (8.19 g, 48.26 mmol) are added to di-tert-butyl (1S,2R,3S,4R,5R,6R)-2-[(tert-butoxycarbonyl)amino]-3-[(3,4-dichlorobenzyl)oxy]-4-hydroxybicyclo[3.1.0]hexane-2,6-dicarboxylate (14.20 g, 24.13 mmol) and tetrahydrofuran (241.28 mL, 2.97 moles) at room temperature. Cool the mixture in an ice bath. Diisopropyl azodicarboxylate (9.57 mL, 9.76 g, 48.26 mmol) in tetrahydrofuran (20 mL) is added and the reaction mixture is gradually warmed to room temperature overnight. Dilute with diethyl ether, and then wash with aqueous sodium carbonate. Extract the aqueous layer again with diethyl ether. Combine all ether extracts, wash with water, brine, dry over magnesium sulfate, and concentrate under reduced pressure to give a residue. The residue is purified by flash chromatography, eluting with 10-100% ethyl acetate in hexanes to give the title compound (9 g, 12.2 mmol, 51%): MS (m/z): 759 (M+1).

Preparation 7: Di-tert-butyl (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate

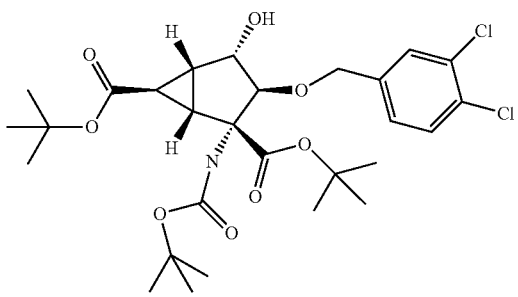

Potassium carbonate (5.11 g, 36.60 mmol) is added to a solution of di-tert-butyl (1S,2R,3S,4S,5R,6R)-2-[(tert-butoxycarbonyl)amino]-3-[(3,4-dichlorobenzyl)oxy]-4-{[(4-nitrophenyl)carbonyl]oxy}bicyclo[3.1.0]hexane-2,6-dicarboxylate (9.00 g, 12.20 mmol) and methanol (122.01 mL, 3.01 moles), and then stirred at room temperature. After 1 hour, dilute the reaction mixture with ethyl acetate, wash with water (75 mL), brine (75 mL), dry over sodium sulfate, and concentrate under reduced pressure to give a residue. The residue is purified by flash chromatography, eluting with 10-60% ethyl acetate:hexanes to give the title compound (5.3 g, 9.01 mmol, 74%). MS (m/z): 610/612 (M+1).

Preparation 8: Di-tert-butyl (1S,2R,3S,4R,5R,6R)-2-[(tert-butoxycarbonyl)amino]-3-[(3,4-dichlorobenzyl)oxy]-4-[(methylsulfonyl)oxy]bicyclo[3.1.0]hexane-2,6-dicarboxylate

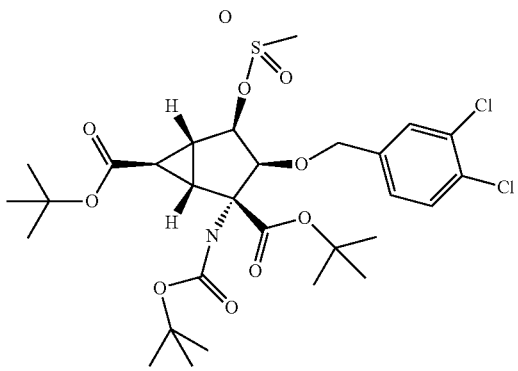

Methanesulfonyl chloride (0.841 mL, 1.25 g, 10.87 mmol) is added to di-tert-butyl (1S,2R,3S,4R,5R,6R)-2-[(tert-butoxycarbonyl)amino]-3-[(3,4-dichlorobenzyl)oxy]-4-hydroxybicyclo[3.1.0]hexane-2,6-dicarboxylate (2.00 g, 3.40 mmol), triethylamine (1.66 mL, 1.20 g, 11.89 mmol), and tetrahydrofuran (33.98 mL, 30.11 g, 417.61 mmol) at 0° C. and stirred. Gradually warm the reaction to room temperature and stir overnight. Dilute the reaction with saturated aqueous sodium bicarbonate then extract with ethyl acetate (3×100 mL). The combined organic extracts are washed with brine, dried over magnesium sulfate, filtered, and then concentrated under reduced pressure to yield a residue. The residue is purified by flash chromatography using eluting with 5-60% ethyl acetate in hexanes to give the title compound (1.40 g, 2.10 mmol, 62%).

Preparation 9: Di-tert-butyl (1R,2R,3S,4S,5R,6R)-2-[(tert-butoxycarbonyl)amino]-3-[(3,4-dichlorobenzyl)oxy]-4-(1H-1,2,4-triazol-3-ylsulfanyl)bicyclo[3.1.0]hexane-2,6-dicarboxylate

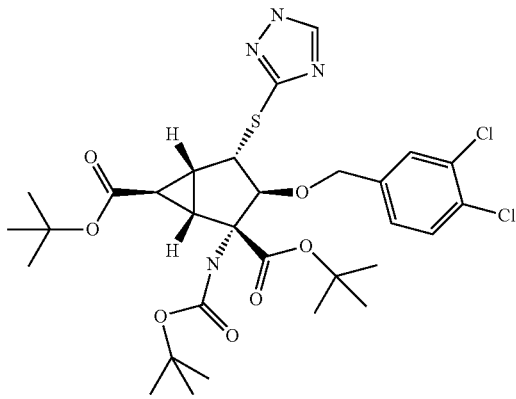 [SMILES: CC(C)(C)OC(=O)N[C@]1(C(=O)OC(C)(C)C)[C@@H]2[C@@H](C(=O)OC(C)(C)C)[C@@H]2[C@H](Sc2nc[nH]n2)[C@H]1OCc1ccc(Cl)c(Cl)c1]

Potassium carbonate (1.45 g, 10.50 mmol) is added to 1H-1,2,4-triazole-3-thiol (424.79 mg, 4.20 mmol) and dimethylformamide (10.50 mL, 9.93 g, 135.80 mmol) at room temperature and stirred. After 5 minutes, di-tert-butyl (1S,2R,3S,4R,5R,6R)-2-[(tert-butoxycarbonyl)amino]-3-[(3,4-dichlorobenzyl)oxy]-4-[(methylsulfonyl)oxy]bicyclo[3.1.0]hexane-2,6-dicarboxylate (1.40 g, 2.10 mmol) is added to the reaction and stirred at 85° C. After 2 days, cool the reaction to room temperature, dilute with saturated sodium bicarbonate, then extract with ethyl acetate (3×). The combined organics are washed with water, brine, filtered, and concentrated under reduced pressure to give a residue. The residue is purified by flash chromatography eluting with 5-75% ethyl acetate in hexanes to give the title compound (978.0 mg, 1.46 mmol, 69%). MS (m/z): 671/669 (M−1).

Preparation 10: Di-tert-butyl (1R,2R,3S,4S,5R,6R)-2-[(tert-butoxycarbonyl)amino]-3-[(3,4-dichlorobenzyl)oxy]-4-(1,3-thiazol-2-ylsulfanyl)bicyclo[3.1.0]hexane-2,6-dicarboxylate

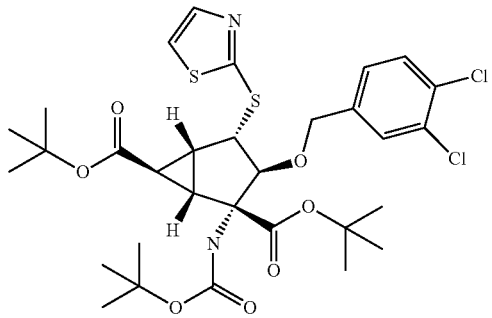 [SMILES: CC(C)(C)OC(=O)N[C@]1(C(=O)OC(C)(C)C)[C@@H]2[C@@H](C(=O)OC(C)(C)C)[C@@H]2[C@H](Sc2nccs2)[C@H]1OCc1ccc(Cl)c(Cl)c1]

This compound is prepared essentially as described in Preparation 9 by using 2-mercaptothiazole. Residue is purified by normal phase chromatography to yield 29% of the title compound. MS (m/z): 465 (M+1).

Preparation 11: Di-tert-butyl (1R,2R,3S,4S,5R,6R)-2-[(tert-butoxycarbonyl)amino]-3-[(3,4-dichlorobenzyl)oxy]-4-[(1-methyl-1,2,4-triazol-3-yl)sulfanyl]bicyclo[3.1.0]hexane-2,6-dicarboxylate

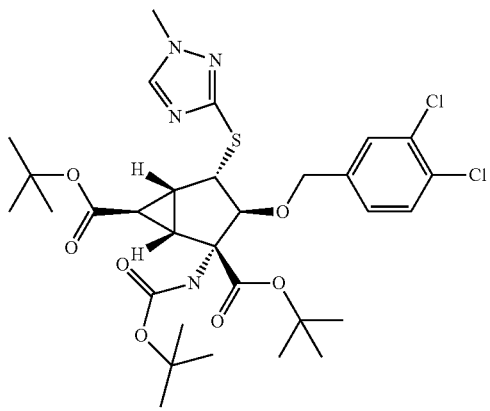 [SMILES: Cn1cnc(S[C@H]2[C@H]3[C@H](C(=O)OC(C)(C)C)[C@H]3[C@](NC(=O)OC(C)(C)C)(C(=O)OC(C)(C)C)[C@@H]2OCc2ccc(Cl)c(Cl)c2)n1]

Dissolve di-tert-butyl (1R,2R,3S,4S,5R,6R)-2-[(tert-butoxycarbonyl)amino]-3-[(3,4-dichlorobenzyl)oxy]-4-(1H-1,2,4-triazol-3-ylsulfanyl)bicyclo[3.1.0]hexane-2,6-dicarboxylate (0.60 g, 0.893 mmol) in anhydrous tetrahydrofuran (3.6 mL) in a flame-dried flask and cool to −78° C. Add potassium t-butoxide (0.80 g, 0.893 mmol) and stir for 15 minutes. Add methyl iodide (0.127 g, 0.893 mmol, pretreated by filtration through basic alumina) and allow to stir at −78° C. for 15 minutes. Allow the mixture to warm to room temperature and then stir for 30 minutes at room temperature. Pour crude reaction mixture into water and adjust pH to 6 with 1N aqueous HCl and extract into ethyl acetate. Dry the organic layer over magnesium sulfate, filter and concentrate under reduced pressure. Purify by reverse phase flash chromatography (100 g C18 column eluting with 45-95% Acetonitrile/Water (with 0.1% trifluoroacetic acid in both), compound elutes at 89% Acetonitrile). Combine the desired fractions and neutralize with aqueous bicarbonate. Extract with ethyl acetate, dry the organic layer over magnesium sulfate, filter and concentrate under reduced pressure to yield the title compound as a white foam (0.16 g, 0.23 mmol, 26%): MS (m/z): 473/475/477 (M+1).

Preparation 12: Di-tert-butyl (1S,2R,3R,4S,5R,6S)-4-azido-2-[(tert-butoxycarbonyl)amino]-3-[(3,4-dichlorobenzyl)oxy]bicyclo[3.1.0]hexane-2,6-dicarboxylate

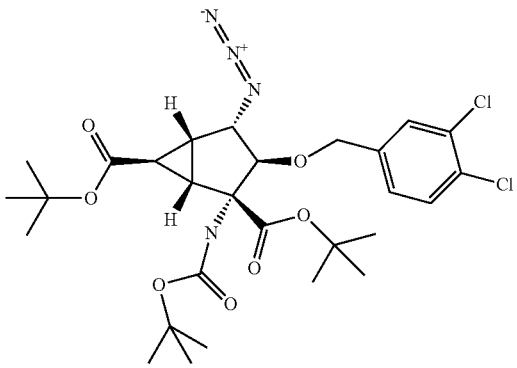

Sodium azide (8.29 g, 127.45 mmol) is added to di-tert-butyl (1S,2R,3S,4R,5R,6R)-2-[(tert-butoxycarbonyl)amino]-3-[(3,4-dichlorobenzyl)oxy]-4-[(methylsulfonyl)oxy]bicyclo[3.1.0]hexane-2,6-dicarboxylate (16.99 g, 25.49 mmol) and 15-crown-5 (508.57 μL, 561.46 mg, 2.55 mmol) in dimethylformamide (254.90 mL, 240.96 g, 3.30 moles) at 85° C. and stirred. After 7 days, the reaction is cooled to room temperature then diluted with water and extracted with ethyl acetate (3×). The combined organics are washed with water, brine, dried over magnesium sulfate, filtered, and concentrated under reduced pressure giving a residue. The residue is purified by flash chromatography eluting 2-60% ethyl acetate in hexanes to yield the title compound (11.2 g, 18.3 mmol, 72%). MS (m/z): 635/637 (M+1).

Preparation 13: Di-tert-butyl (1S,2R,3R,4S,5R,6S)-4-amino-2-[(tert-butoxycarbonyl)amino]-3-[(3,4-dichlorobenzyl)oxy]bicyclo[3.1.0]hexane-2,6-dicarboxylate

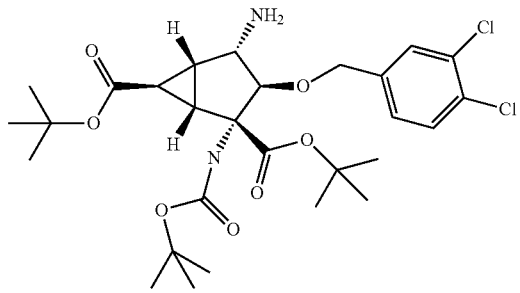 [SMILES: CC(C)(C)OC(=O)N[C@]1(C(=O)OC(C)(C)C)[C@@H]2[C@@H](C(=O)OC(C)(C)C)[C@@H]2[C@H](N)[C@H]1OCc1ccc(Cl)c(Cl)c1]

Add a 1M solution of trimethylphosphine in tetrahydrofuran (19.56 mL, 19.56 mmol) to di-tert-butyl (1S,2R,3R,4S,5R,6S)-4-azido-2-[(tert-butoxycarbonyl)amino]-3-[(3,4-dichlorobenzyl)oxy]bicyclo[3.1.0]hexane-2,6-dicarboxylate (8.00 g, 13.04 mmol) in tetrahydrofuran (43.46 mL) and water (130.39 mL) at room temperature and stir overnight. Saturated aqueous sodium bicarbonate is added to the reaction then extracted with ethyl acetate (3×). The combined organics are washed with brine, dried over magnesium sulfate, filtered, and concentrated under reduced pressure giving the title compound (7.42 g, 12.63 mmol, 97%). MS (m/z): 609/611 (M+Na).

Preparation 14: Di-tert-butyl (1S,2R,3R,4S,5R,6S)-4-(acetylamino)-2-[(tert-butoxycarbonyl)amino]-3-[(3,4-dichlorobenzyl)oxy]bicyclo[3.1.0]hexane-2,6-dicarboxylate

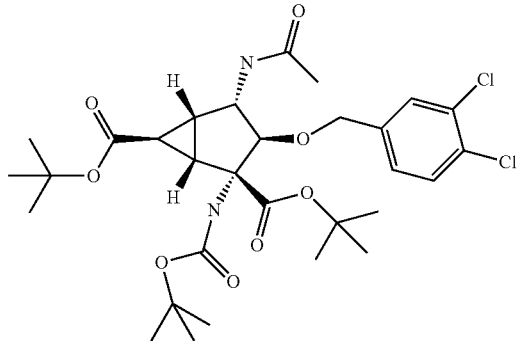 [SMILES: CC(=O)N[C@H]1[C@H]2[C@H](C(=O)OC(C)(C)C)[C@H]2[C@](NC(=O)OC(C)(C)C)(C(=O)OC(C)(C)C)[C@@H]1OCc1ccc(Cl)c(Cl)c1]

Acetyl chloride (334.31 μL, 368.75 mg, 4.70 mmol) in dichloromethane (5 mL) is added to a stirring, cooled solution of di-tert-butyl (1S,2R,3R,4S,5R,6S)-4-amino-2-[(tert-butoxycarbonyl)amino]-3-[(3,4-dichlorobenzyl)oxy]bicyclo[3.1.0]hexane-2,6-dicarboxylate (2.30 g, 3.91 mmol) and triethylamine (709.32 μL, 514.97 mg, 5.09 mmol) in dichloromethane (19.57 mL) at 0° C. then stirred. After 90 minutes, dilute with water and extract with dichloromethane (3×25 mL). The combined organic extracts are dried over magnesium sulfate, filtered, and concentrated under reduced pressure giving the title compound (2.40 g, 3.81 mmol, 97%): MS (m/z): 653 (M+1).

Preparation 15: Di-tert-butyl (1S,2R,3R,4S,5R,6S)-2-[(tert-butoxycarbonyl)amino]-3-[(3,4-dichlorobenzyl)oxy]-4-[(methoxycarbonyl)amino]bicyclo[3.1.0]hexane-2,6-dicarboxylate

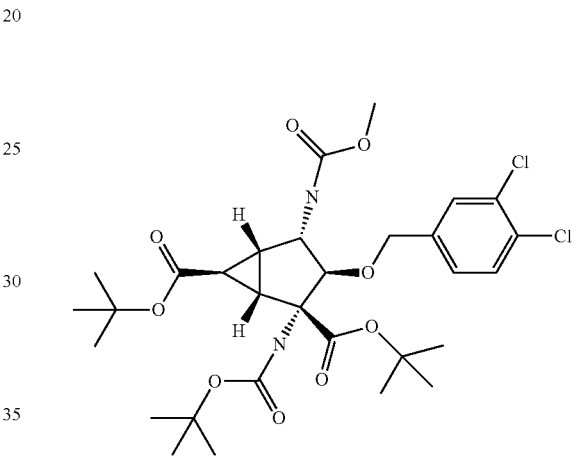

This compound is prepared essentially as described in Preparation 14 by using methyl chloroformate to yield 88% of the title compound.

Preparation 16: Di-tert-butyl (1R,2R,3S,4S,5R,6R)-2-(tert-butoxycarbonylamino)-3-[(3,4-dichlorophenyl)methoxy]-4-[(2-methyl-1,2,4-triazol-3-yl)sulfanyl]bicyclo[3.1.0]hexane-2,6-dicarboxylate

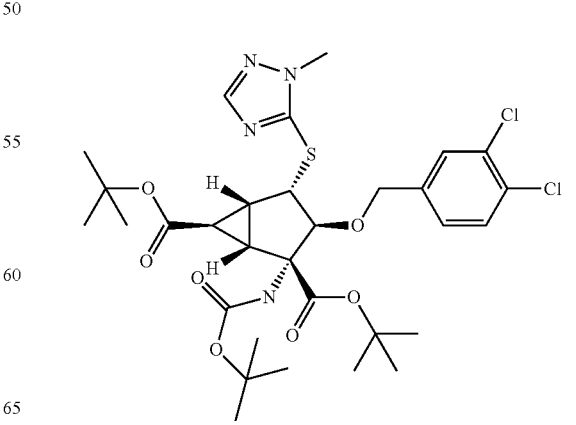

Add 2-methyl-1H-1,2,4-triazole-3-thione (0.126 g, 1.09 mmol) and potassium carbonate (0.35 g, 2.52 mmol) to a solution of di-tert-butyl (1S,2R,3S,4R,5R,6R)-2-[(tert-butoxycarbonyl)amino]-3-[(3,4-dichlorobenzyl)oxy]-4-[(methylsulfonyl)oxy]bicyclo[3.1.0]hexane-2,6-dicarboxylate (0.80 g, 0.84 mmol) in dimethylformamide (1.68 mL. After heating for 2 days at 80° C., pour the solution into brine and extract with ethyl acetate three times, dry the combined organic phases with sodium sulfate, filter and concentrate under reduced pressure. Purify by flash chromatography eluting with 10% ethyl acetate/$CH_2Cl_2$ to yield the title compound as an oil (0.576 g, 0.84 mmol, 100%). MS (m/z): 685/687/689 (M+1).

Preparation 17: Ditert-butyl (1R,2R,3S,4S,5R,6R)-2-(tert-butoxycarbonylamino)-3-[(3,4-dichlorophenyl)methoxy]-4-(1H-imidazol-2-ylsulfanyl)bicyclo[3.1.0]hexane-2,6-dicarboxylate

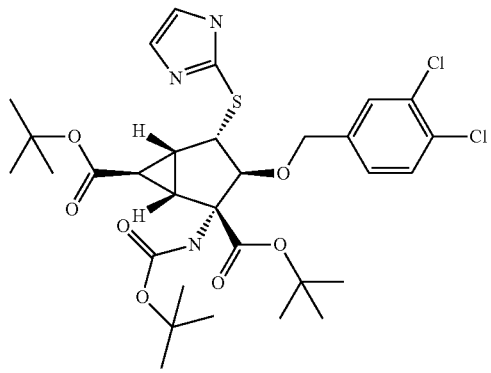 [SMILES: CC(C)(C)OC(=O)N[C@]1(C(=O)OC(C)(C)C)[C@@H]2[C@@H](C(=O)OC(C)(C)C)[C@@H]2[C@H](Sc2ncc[nH]2)[C@H]1OCc1ccc(Cl)c(Cl)c1]

This compound is prepared essentially as described in Preparation 20 by using di-tert-butyl (1S,2R,3 S,4R,5R,6R)-2-[(tert-butoxycarbonyl)amino]-3-[(3,4-dichlorobenzyl)oxy]-4-[(methylsulfonyl)oxy]bicyclo[3.1.0]hexane-2,6-dicarboxylate. Purify by flash chromatography eluting with 30-50% ethyl acetate:hexanes to yield the title compound in 38% yield. MS (m/z): 671/673/675 (M+1).

Preparation 18: Diethyl (1S,2R,3R,4S,5R,6S)-4-[(2-acetoxyacetyl)amino]-2-(tert-butoxycarbonylamino)-3-[(3,4-dichlorophenyl)methoxy]bicyclo[3.1.0]hexane-2,6-dicarboxylate

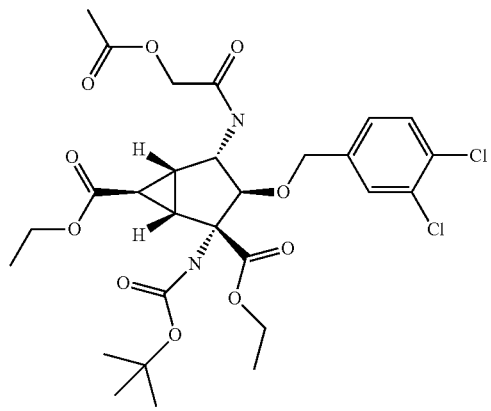 [SMILES: CCOC(=O)[C@H]1[C@@H]2[C@H](NC(=O)COC(C)=O)[C@@H](OCc3ccc(Cl)c(Cl)c3)[C@@](NC(=O)OC(C)(C)C)(C(=O)OCC)[C@H]12]

Add acetoxyacetyl chloride (0.116 mL, 1.08 mmol) to a solution of diethyl (1S,2R,3R,4S,5R,6S)-4-amino-2-(tert-butoxycarbonylamino)-3-[(3,4-dichlorophenyl)methoxy]bicyclo[3.1.0]hexane-2,6-dicarboxylate (0.47 g, 0.89 mmol) and diisoproylethylamine (0.32 mL, 1.83 mmol) in dichloromethane (9 mL) at room temperature. After 2.5 hours, wash the solution with saturated $NaHCO_3$ (2×), brine (1×), dry over $MgSO_4$, filter, and conc. under reduced pressure. Purify by flash chromatography eluting with a gradient of 0 to 100% ethyl acetate in hexanes over 30 min. to yield the title compound as a white solid (0.43 g, 0.68 mmol, 76%). MS (m/z): 531 (M+H-BOC).

Preparation 19: (1S,2R,3R,4S,5R,6S)-2-(tert-butoxycarbonylamino)-3-[(3,4-dichlorophenyl)methoxy]-4-[(2-hydroxyacetyl)amino]bicyclo[3.1.0]hexane-2,6-dicarboxylic acid

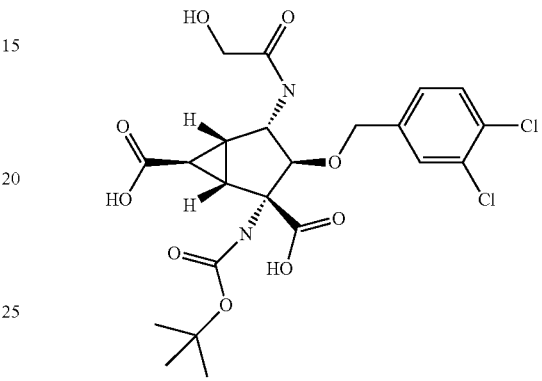

Add 1M aqueous lithium hydroxide (4.0 mL, 4.0 mmol) to a solution of diethyl (1S,2R,3R,4S,5R,6S)-4-[(2-acetoxyacetyl)amino]-2-(tert-butoxycarbonylamino)-3-[(3,4-dichlorophenyl)methoxy]bicyclo[3.1.0]hexane-2,6-dicarboxylate (0.42 g, 0.67 mmol) in tetrahydrofuran (7.0 mL) at room temperature and stir overnight. Acidify the reaction to approximately pH 1 with 5N aqueous HCl. Extract with ethyl acetate (3×25 mL). Dry the combined organic layers, filter, and conc. under reduced pressure. HPLC analysis of crude reaction mixture shows starting material present. Add a 1M aqueous lithium hydroxide (4.0 mL, 4.0 mmol) to a solution of the crude reaction mixture in tetrahydrofuran (7.0 mL) and heat at 50° C. After 17 hours, acidify reaction to approximately pH 1 with 5N aqueous HCl. Extract with ethyl acetate (3×25 mL). Dry the combined extracts, filter, and conc. under reduced pressure. Purify by preparative reverse-phase high performance liquid chromatography using a gradient of 95% water (with 0.03% HCl)/5% acetonitrile to 5% water (with 0.03% HCl)/95% acetonitrile over 40 min. to provide (1S,2R,3R,4S,5R,6S)-2-(tert-butoxycarbonylamino)-3-[(3,4-dichlorophenyl)methoxy]-4-[(2-hydroxyacetyl)amino]bicyclo[3.1.0]hexane-2,6-dicarboxylic acid (0.181 g, 0.34 mmol, 51%) as a white solid. MS (m/z): 531 (M−H).

Preparation 20: (1S,2R,3S,4S,5R,6R)-2-[(Tert-butoxycarbonyl)amino]-3-[(3,4-dichlorobenzyl)oxy]-4-hydroxybicyclo[3.1.0]hexane-2,6-dicarboxylic acid

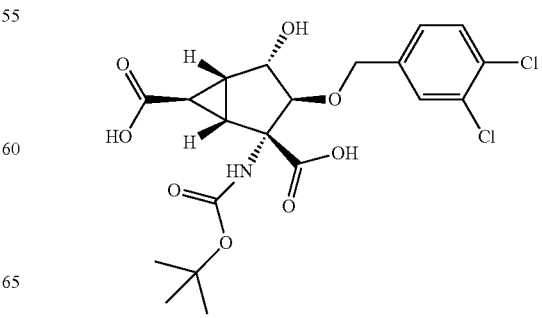

Dissolve (1S,2R,3S,4S,5R,6R)-2-amino-3-[(3,4-dichlorobenzyl)oxy]-4-hydroxybicyclo[3.1.0]hexane-2,6-dicarboxylic acid (2 g, 5.32 mmol) in dioxane (10.63 mL), then treat with saturated aqueous sodium bicarbonate (10.63 mL, 6.90 mmol) and di-tert-butyldicarbonate (5.80 g, 26.58 mmol). Stir the biphasic mixture at room temperature for 18 days, then concentrate to remove solvent. Dissolve the resulting residue in acetonitrile (assisting with 1N HCl), and extract twice to remove di-tert-butyldicarbonate. Concentrate the acetonitrile layer. Dissolve the resulting residue in ethyl acetate, then wash twice with 1N HCl, wash once with brine, dry over sodium sulfate, and concentrate to dryness to give the title compound (2.1 g, 4.41 mmol, 83%). MS (m/z): 474 (M−1).

Preparation 21: (1S,2R,3R,4S,5R,6S)-4-(acetylamino)-2-[(tert-butoxycarbonyl)amino]-3-[(3,4-dichlorobenzyl)oxy]bicyclo[3.1.0]hexane-2,6-dicarboxylic acid

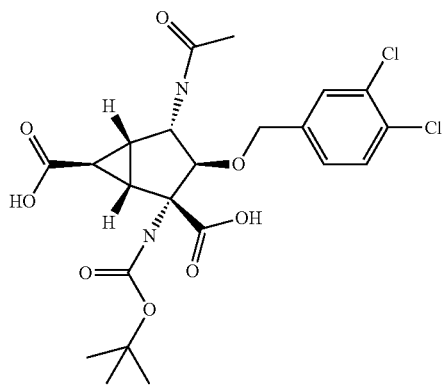 [SMILES: CC(=O)N[C@H]1[C@H]2[C@H](C(=O)O)[C@H]2[C@](NC(=O)OC(C)(C)C)(C(=O)O)[C@@H]1OCc1ccc(Cl)c(Cl)c1]

This compound is prepared essentially as described in Preparation 20 by using (1S,2R,3R,4S,5R,6S)-4-(acetylamino)-2-amino-3-[(3,4-dichlorobenzyl)oxy]bicyclo[3.1.0]hexane-2,6-dicarboxylic acid to yield the title compound in 74% yield. MS (m/z): 515/517 (M−1).

Preparation 22: Bis({[(1-methylethoxy)carbonyl]oxy}methyl)(1S,2R,3 S,4S,5R,6R)-2-[(tert-butoxycarbonyl)amino]-3-[(3,4-dichlorobenzyl)oxy]-4-hydroxybicyclo[3.1.0]hexane-2,6-dicarboxylate

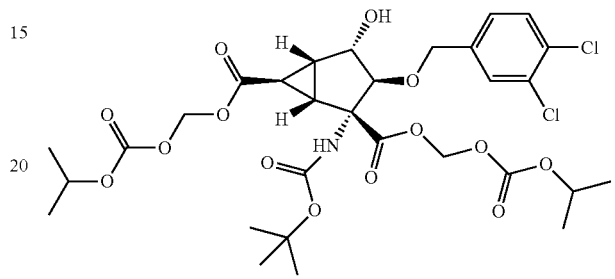

To a solution of (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylic acid (1.89 g, 3.96 mmol) in dimethylformamide (23.3 mL) is added chloromethyl isopropyl carbonate (1.27 g, 8.33 mmol), sodium iodide (59.4 mg, 0.396 mmol), and cesium carbonate (2.84 g, 8.72 mmol). Stir the mixture overnight at room temperature under nitrogen. Dilute the reaction mixture with ethyl acetate and water. Separate the layers. Extract the aqueous layer twice with ethyl acetate. Extract the combined organic layers with brine, dry over magnesium sulfate, filter and concentrate. Purify the residue by flash chromatography eluting with 0 to 75% ethyl acetate in hexane to yield the title compound as a foam (940 mg, 1.33 mmol, 33%). MS (m/z): 732 (M+Na).

The compounds of Preparation 23-26 may be prepared essentially as described in Preparation 22:

| Prep. No. | Chemical Name | Structure | Yield (%) | Physical Data MS(m/z) |
|---|---|---|---|---|
| 23 | Bis{[(ethoxycarbonyl)oxy]methyl}(1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate | 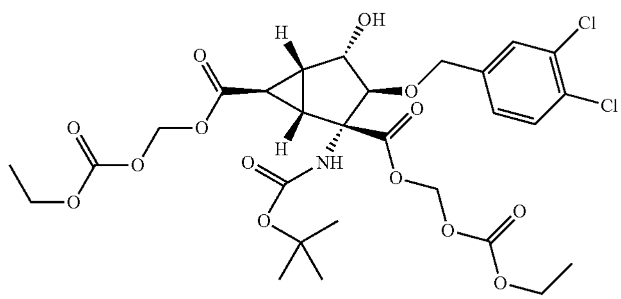 | Absolute 58 | 702 (M + Na) |

-continued

| Prep. No. | Chemical Name | Structure | Yield (%) | Physical Data MS(m/z) |
|---|---|---|---|---|
| 24 | Bis{[(cyclopropylcarbonyl)oxy]methyl} (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate | 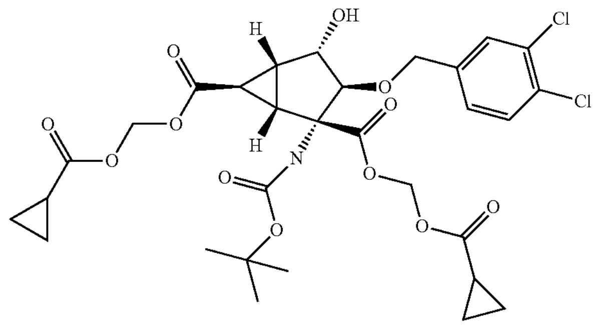 [SMILES: CC(C)(C)OC(=O)N[C@]1(C(=O)OCOC(=O)C2CC2)[C@@H]2[C@@H](C(=O)OCOC(=O)C3CC3)[C@@H]2[C@H](O)[C@H]1OCc1ccc(Cl)c(Cl)c1] | 55 | 694/696 (M + Na) |
| 25 | Bis{[(2-methylpropanoyl)oxy]methyl} (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate | 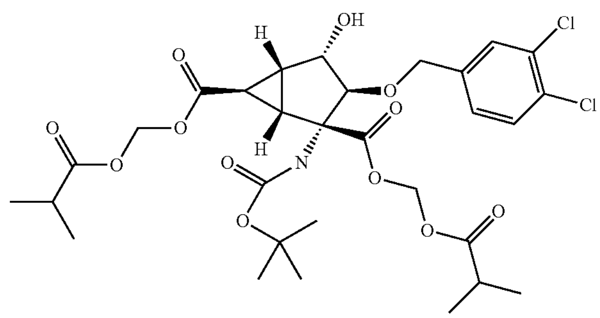 [SMILES: CC(C)C(=O)OCOC(=O)[C@H]1[C@@H]2[C@H](O)[C@@H](OCc3ccc(Cl)c(Cl)c3)[C@@](NC(=O)OC(C)(C)C)(C(=O)OCOC(=O)C(C)C)[C@H]12] | 49 | 698/700 (M + Na) |
| 26 | Bis[(acetyloxy)methyl] (1S,2R,3R,4S,5R,6S)-4-(acetylamino)-2-[(tert-butoxycarbonyl)amino]-3-[(3,4-dichlorobenzyl)oxy]bicyclo[3.1.0]hexane-2,6-dicarboxylate | 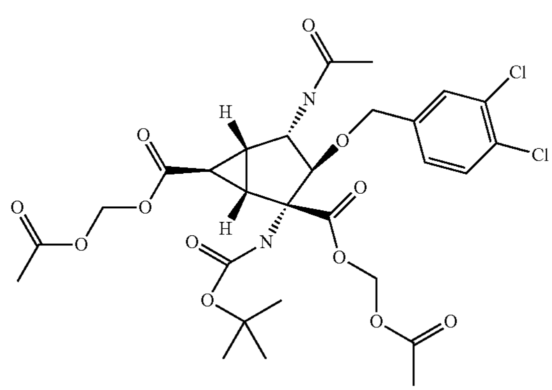 [SMILES: CC(=O)N[C@H]1[C@H]2[C@H](C(=O)OCOC(C)=O)[C@H]2[C@](NC(=O)OC(C)(C)C)(C(=O)OCOC(C)=O)[C@@H]1OCc1ccc(Cl)c(Cl)c1] | | |

EXAMPLE 1

(1S,2R,3S,4S,5R,6R)-2-Amino-3-[(3,4-dichlorobenzyl)oxy]-4-hydroxybicyclo[3.1.0]hexane-2,6-dicarboxylic acid

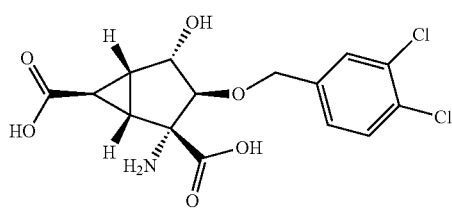 [SMILES: N[C@]1(C(=O)O)[C@@H]2[C@@H](C(=O)O)[C@@H]2[C@H](O)[C@H]1OCc1ccc(Cl)c(Cl)c1]

Di-tert-butyl (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate (5.30 g, 9.01 mmol) is added to water (30.02 mL) and acetic acid (30.02 mL). Heat the reaction at reflux until the complete consumption of the starting material. Cool and concentrate on a rotary evaporator. Triturate the concentrate with diethyl ether, collect the precipitate, then dry in a vacuum oven to give the title compound (3.30 g, 8.77 mmol, 97%). MS (m/z): 376/378 (M+1).

The compounds of Example 2-3 may be prepared essentially as described in Example 1:

EXAMPLE 4

(1S,2R,3R,4S,5R,6S)-4-(Acetylamino)-2-amino-3-[(3,4-dichlorobenzyl)oxy]bicyclo[3.1.0]hexane-2,6-dicarboxylic acid

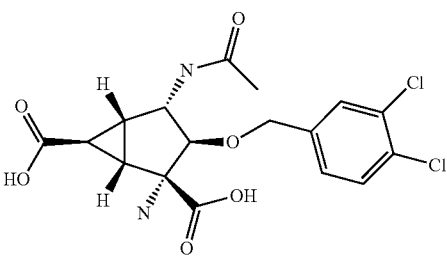 [SMILES: CC(=O)N[C@H]1[C@H]2[C@H](C(=O)O)[C@H]2[C@](N)(C(=O)O)[C@@H]1OCc1ccc(Cl)c(Cl)c1]

Di-tert-butyl (1S,2R,3R,4S,5R,6S)-4-(acetylamino)-2-[(tert-butoxycarbonyl)amino]-3-[(3,4-dichlorobenzyl)oxy]bicyclo[3.1.0]hexane-2,6-dicarboxylate (2.40 g, 3.81 mmol) is added to acetic acid (7.99 g, 7.62 mL, 133.05 mmol,) and water (3.81 mL, 3.81 g, 211.60 mmol) and heated in a microwave to 140° C. After 15 minutes, cool to room temperature, dilute with water and filter to collect the solids. Sequentially wash the solids with water (2×50 mL) and diethyl ether (2×50

| Ex No. | Chemical Name | Structure | Yield (%) | Physical Data MS(m/z) |
|---|---|---|---|---|
| 2 | (1R,2R,3S,4S,5R,6R)-2-Amino-3-[(3,4-dichlorobenzyl)oxy]-4-(1H-1,2,4-triazol-3-ylsulfanyl)bicyclo[3.1.0]hexane-2,6-dicarboxylic acid | 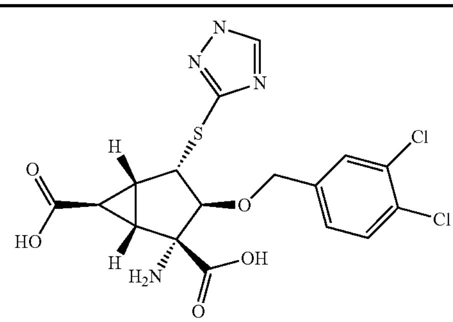 | 81 | MS (m/z): 459/461 (M + 1) |
| 3 | (1R,2R,3S,4S,5R,6R)-2-Amino-3-[(3,4-dichlorobenzyl)oxy]-4-(1,3-thiazol-2-ylsulfanyl)bicyclo[3.1.0]hexane-2,6-dicarboxylic acid | | 73 | MS (m/z): 475/477 (M + 1) | mL), and then dry in a vacuum oven giving the title compound (1.23 g, 2.95 mmol, 77%): MS (m/z): 417/419 (M+1).

EXAMPLE 5

(1S,2R,3R,4S,5R,6S)-2-Amino-3-[(3,4-dichlorobenzyl)oxy]-4-[(methoxycarbonyl)amino]bicyclo[3.1.0]hexane-2,6-dicarboxylic acid

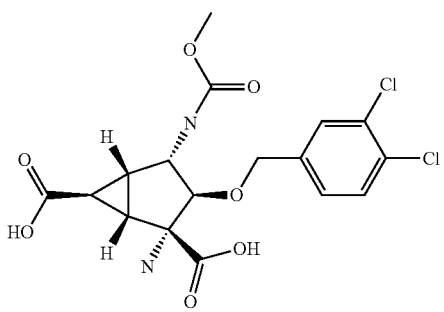 [SMILES: COC(=O)N[C@H]1[C@H]2[C@H](C(=O)O)[C@H]2[C@](N)(C(=O)O)[C@@H]1OCc1ccc(Cl)c(Cl)c1]

This compound is prepared essentially as described in Example 4 by using (1S,2R,3R,4S,5R,6S)-2-amino-3-[(3,4-dichlorobenzyl)oxy]-4-[(methoxycarbonyl)amino]bicyclo[3.1.0]hexane-2,6-dicarboxylic acid. 81% yield. MS (m/z): 433/435 (M+1).

EXAMPLE 6

(1R,2R,3S,4S,5R,6R)-2-amino-3-[(3,4-dichlorobenzyl)oxy]-4-[(1-methyl-1H-1,2,4-triazol-5-yl)sulfanyl]bicyclo[3.1.0]hexane-2,6-dicarboxylic acid hydrochloride

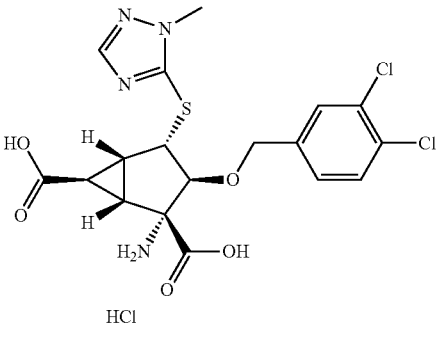 [SMILES: Cn1ncnc1S[C@H]1[C@H]2[C@H](C(=O)O)[C@H]2[C@](N)(C(=O)O)[C@@H]1OCc1ccc(Cl)c(Cl)c1 ; Cl]

Add acetic acid (2.0 mL) and water (2.0 mL) to di-tert-butyl (1R,2R,3S,4S,5R,6R)-2-(tert-butoxycarbonylamino)-3-[(3,4-dichlorophenyl)methoxy]-4-[(2-methyl-1,2,4-triazol-3-yl)sulfanyl]bicyclo[3.1.0]hexane-2,6-dicarboxylate (0.305 g, 0.445 mmol) in a microwave vessel and seal and heat the mixture to 140° C. for 25 minutes. Cool and concentrate the mixture to dryness, and then add 5 N hydrochloric acid (2 mL), acetonitrile (2 mL), and transfer to a vial. Lyophilize overnight to yield the title compound as a white solid (0.227 g, 0.445 mmol; 95%): MS (m/z): 473/475/477 (M+1).

The compounds of Example 7-8 may be prepared essentially as described in Example 6:

| Ex. No. | Chemical Name | Structure | Yield (%) | Physical Data MS(m/z) |
|---|---|---|---|---|
| 7 | (1R,2R,3S,4S,5R,6R)-2-Amino-3-[(3,4-dichlorophenyl)methoxy]-4-[(1-methyl-1,2,4-triazol-3-yl)sulfanyl]bicyclo[3.1.0]hexane-2,6-dicarboxylic acid hydrochloride. | 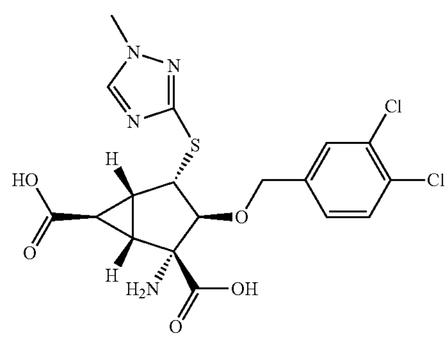 | 91 | 473/475/477 (M + 1). |
| 8 | (1R,2R,3S,4S,5R,6R)-2-Amino-3-[(3,4-dichlorobenzyl)oxy]-4-(1H-imidazol-2-ylsulfanyl)bicyclo[3.1.0]hexane-2,6-dicarboxylic acid hydrochloride | 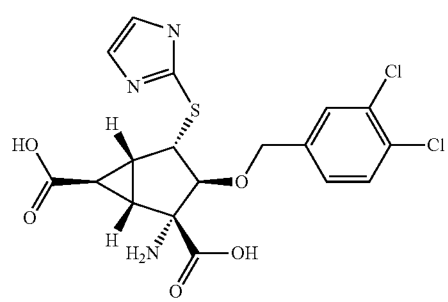 | 88 | 458/460/462 (M + 1) |

EXAMPLE 9

(1S,2R,3R,4S,5R,6S)-2-Amino-3-[(3,4-dichlorobenzyl)oxy]-4-[(hydroxyacetyl)amino]bicyclo[3.1.0]hexane-2,6-dicarboxylic acid hydrochloride

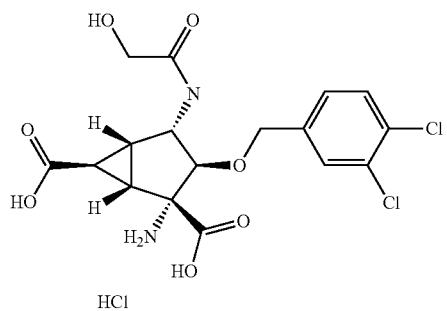 [SMILES: N[C@]1(C(=O)O)[C@@H]2[C@@H](C(=O)O)[C@@H]2[C@H](NC(=O)CO)[C@H]1OCc1ccc(Cl)c(Cl)c1 ; Cl]

HCl

Add 4N hydrogen chloride (3.0 mL, 12.0 mmol) in 1,4-dioxane to a mixture of (1S,2R,3R,4S,5R,6S)-2-(tert-butoxycarbonylamino)-3-[(3,4-dichlorophenyl)methoxy]-4-[(2-hydroxyacetyl)amino]bicyclo[3.1.0]hexane-2,6-dicarboxylic acid (0.032 g, 0.06 mmol) in water (0.3 mL). Wash the solid with acetonitrile and diethylether on a fritted funnel Sequentially wash the solid with acetonitrile and diethylether and then further dry in a vacuum oven overnight at 50° C. to provide the title compound as a white solid (0.018 g, 0.04 mmol, 65%). MS (m/z): 433 (M+H).

EXAMPLE 10

Bis({[(1-methylethoxy)carbonyl]oxy}methyl) (1S,2R,3S,4S,5R,6R)-2-amino-3-[(3,4-dichlorobenzyl)oxy]-4-hydroxybicyclo[3.1.0]hexane-2,6-dicarboxylate hydrochloride

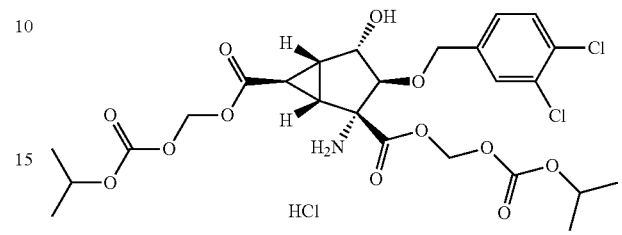

HCl

Add bis({[(1-methylethoxy)carbonyl]oxy}methyl) (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate in a 4.0M solution of hydrogen chloride in dioxane (14.47 mL, 57.87 mmol) and stir for 45 minutes. Add ethyl acetate, and concentrate the reaction mixture to a foam. Triturate the foam with ethyl acetate to produce a solid. Concentrate and dry under vacuum at 40° C. overnight to provide the title compound as an off-white solid (1.77 g, 2.75 mmol, 95%): MS (m/z): 608 (M+H).

The compounds of Example 11-14 may be prepared essentially as described in Example 10:

| Ex. No. | Chemical Name | Structure | Yield (%) | Physical Data MS(m/z) |
|---|---|---|---|---|
| 11 | Bis{[(ethoxycarbonyl)oxy]methyl} (1S,2R,3S,4S,5R,6R)-2-amino-3-[(3,4-dichlorobenzyl)oxy]-4-hydroxybicyclo[3.1.0]hexane-2,6-dicarboxylate hydrochloride | 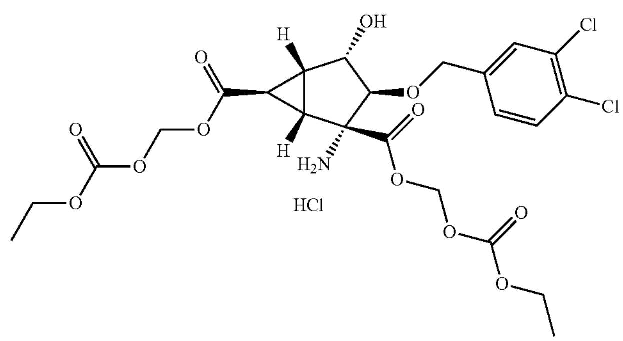 | 97 | 608 (M + 1) |
| 12 | Bis{[(2-methylpropanoyl)oxy]methyl} (1S,2R,3S,4S,5R,6R)-2-amino-3-[(3,4-dichlorobenzyl)oxy]-4-hydroxybicyclo[3.1.0]hexane-2,6-dicarboxylate hydrochloride | 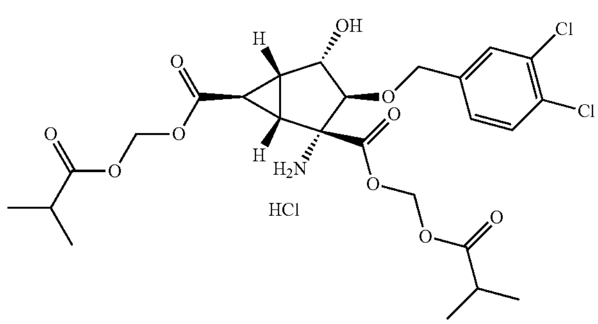 [SMILES: CC(C)C(=O)OCOC(=O)[C@H]1[C@@H]2[C@H](O)[C@@H](OCc3ccc(Cl)c(Cl)c3)[C@@](N)(C(=O)OCOC(=O)C(C)C)[C@H]12 ; Cl] | 73 | 575/577 (M + 1) |

| Ex. No. | Chemical Name | Structure | Yield (%) | Physical Data MS(m/z) |
|---|---|---|---|---|
| 13 | Bis{[(cyclopropylcarbonyl)oxy]methyl} (1S,2R,3S,4S,5R,6R)-2-amino-3-[(3,4-dichlorobenzyl)oxy]-4-hydroxybicyclo[3.1.0]hexane-2,6-dicarboxylate hydrochloride | 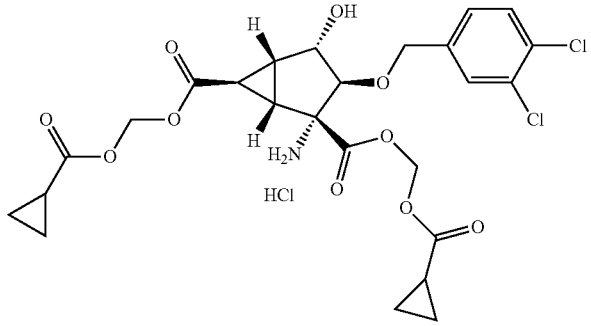 [SMILES: N[C@]1(C(=O)OCOC(=O)C2CC2)[C@@H]2[C@@H](C(=O)OCOC(=O)C3CC3)[C@@H]2[C@H](O)[C@H]1OCc1ccc(Cl)c(Cl)c1 ; Cl] | 97 | 572/574 (M + 1) |
| 14 | Bis[(acetyloxy)methyl] (1S,2R,3R,4S,5R,6S)-4-(acetylamino)-2-amino-3-[(3,4-dichlorobenzyl)oxy]bicyclo[3.1.0]hexane-2,6-dicarboxylate hydrochloride | 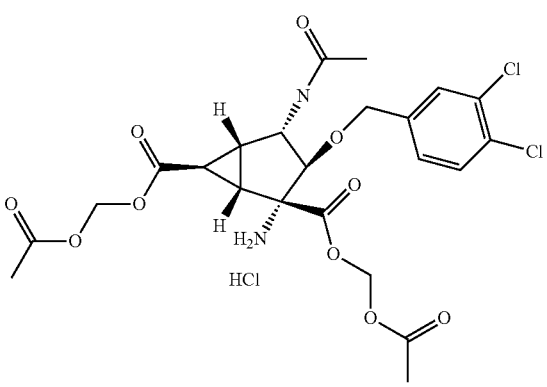 [SMILES: CC(=O)N[C@H]1[C@H]2[C@H](C(=O)OCOC(C)=O)[C@H]2[C@](N)(C(=O)OCOC(C)=O)[C@@H]1OCc1ccc(Cl)c(Cl)c1 ; Cl] | 82 | 561/563 (M + 1) |

EXAMPLE 15

Bis({[(1-methylethoxy)carbonyl]oxy}methyl)(1S,2R,3S,4S,5R,6R)-2-amino-3-[(3,4-dichlorobenzyl)oxy]-4-hydroxybicyclo[3.1.0]hexane-2,6-dicarboxylate hydrochloride

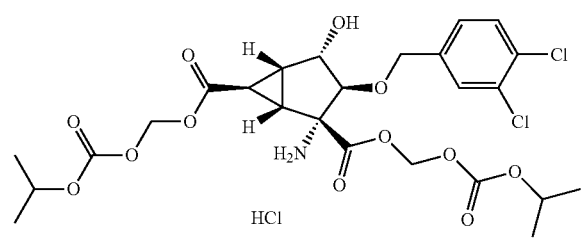 [SMILES: CC(C)OC(=O)OCOC(=O)[C@H]1[C@@H]2[C@H](O)[C@@H](OCc3ccc(Cl)c(Cl)c3)[C@@](N)(C(=O)OCOC(=O)OC(C)C)[C@H]12 ; Cl]

Step 1: Di-tert-butyl (1S,2S,4S,5R,6R)-2-[(tert-butoxycarbonyl)amino]-4-hydroxy-bicyclo[3.1.0]hexane-2,6-dicarboxylate

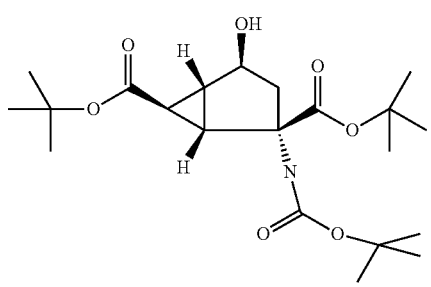 [SMILES: CC(C)(C)OC(=O)N[C@@]1(C(=O)OC(C)(C)C)C[C@H](O)[C@H]2[C@H](C(=O)OC(C)(C)C)[C@H]21]

Add 1M lithium tri(sec-butyl)borohydride in tetrahydrofuran (2.67 L, 2.67 mol) dropwise to a solution of di-tert-butyl (1S,2S,5R,6R)-2-[(tert-butoxycarbonyl)amino]-4-oxobicyclo[3.1.0]hexane-2,6-dicarboxylate (1000 g, 2.43 mol) in dry tetrahydrofuran (10 L) at 0° C. under nitrogen. After 2 hours at 0° C., 2M Na₂CO₃ in water (850 g, 8.02 mol) is added at 0° C. over 2 hours followed by 35% aqueous hydrogen peroxide (740 mL, 8.99 mol) in water (3.3 L). After 40 minutes, the mixture is warmed to ambient temperature whereupon the organic phase is separated. The organic phase is diluted with methyl tert-butyl ether (3.5 L) and the layers are separated again. The aqueous phase is extracted with methyl tert-butyl ether (3.5 L). All the combined organic phases are washed successively with 1M aqueous Na₂SO₃ (2.67 L), water (2.67 L), and brine (2.67 L), dried over sodium sulfate, filtered and concentrated to a volume of 3 L. The precipitated solid is filtered and washed with heptane (1.3 L) to obtain the title compound (864.76 g). The mother liquors are concentrated to dryness and the residue is triturated with heptane (500 mL) and filtered to obtain additional title compound (130.64 g, total 995.4 g, yield 99%). MS (m/z): 436 (M+23).

Step 2: Di-tert-butyl (1S,2S,5R,6S)-2-[(tert-butoxycarbonyl)amino]bicyclo[3.1.0]hex-3-ene-2,6-dicarboxylate

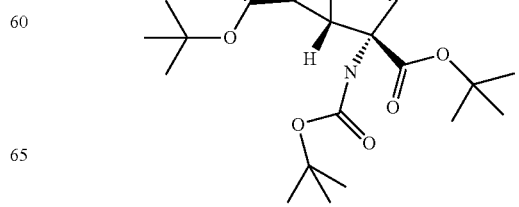

Triethylamine (735 mL, 5.30 mol) is added dropwise at 0° C. under N₂ over 40 minutes to a solution of di-tert-butyl(2S, 4S)-2-[(tert-butoxycarbonyl)amino]-4-hydroxybicyclo [3.1.0]hexane-2,6-dicarboxylate (995.4 g, 2.41 mol) in dry tetrahydrofuran (8.4 L) Methanesulfonyl chloride (373 mL, 4.82 mol) is added at 0° C. over 50 minutes. The reaction is warmed to 23° C. After 3 hours, the reaction if filtered to remove triethylamine hydrochloride salt. Wash the filter cake with dry tetrahydrofuran (2×2 L). The filtrate (13 L) is split into two equal parts. To one half of filtrate, add 1M potassium tert-butoxide in tetrahydrofuran (3.6 L, 3.6 mol) dropwise to the solution obtained in previous step (Crude V=6.5 L, 1.2 mol) at 15° C. over 2 hours 15 minutes then allow to warm to 23° C. After 2 hours 30 minutes the reaction is quenched by pouring into 10% aqueous acetic acid (950 mL). Separate the layers and extract the aqueous layer with ethyl acetate (1.7 L). The organic layers are combined and concentrated in vacuo to obtain a solid which is dissolved in acetone (1.45 L) and added to water (7.3 L). Stir the resulting suspension overnight at 23° C. Filter off the precipitate, wash with water (2×1 L), and dry in the vacuum oven at 40° C. to obtain the title compound (450.67 g, yield 95%). MS (m/z): 418 (M+23).

Step 3: Di-tert-butyl (1S,2R,3S,4R,5R,6R)-2-[(tert-butoxycarbonyl)amino]-3,4-dihydroxybicyclo[3.1.0]hexane-2,6-dicarboxylate

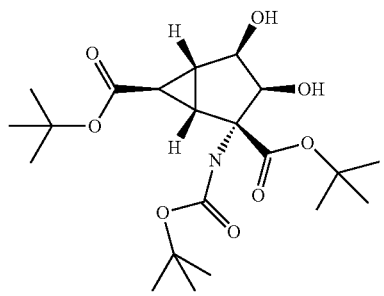 [SMILES: CC(C)(C)OC(=O)N[C@]1(C(=O)OC(C)(C)C)[C@@H]2[C@@H](C(=O)OC(C)(C)C)[C@@H]2[C@@H](O)[C@H]1O]

Osmium tetraoxide (4% wt/wt in water, 231.78 mL, 241.05 g, 37.93 mmol,) is added at 23° C. to a solution of N-methylmorpholine-N-oxide hydrate (101.62 mL; 114.83 g, 424.78 mmol), N-methylmorpholine-N-oxide hydrate (116.88 g, 864.74 mmol), 4-methylmorpholine-4-oxide (198.88 mL; 195.50 g, 1.67 mol), and di-tert-butyl (1S,2S,5R,6S)-2-[(tert-butoxycarbonyl)amino]bicyclo[3.1.0]hex-3-ene-2,6-dicarboxylate (600.00 g, 1.52 mol) in acetone (12.00 L) and water (1.80 L). The mixture is stirred at 23° C. overnight. Thin layer chromatograph (hexane/ethyl acetate 3:2; stain: PMA) analysis of the reaction mixture revealed complete consumption of di-tert-butyl (1S,2S,5R,6S)-2-[(tert-butoxycarbonyl)amino] bicyclo[3.1.0]hex-3-ene-2,6-dicarboxylate. The reaction is quenched with saturated aqueous Na₂S₂O₃ (1 L) and extracted with methyl tert-butyl ether (15 L). The organic phase is washed with an aqueous solution (1.5 L) prepared from 37% aqueous HCl (300 mL) and brine (1.2 L), dried with anhydrous MgSO₄, filtered, and concentrated in vacuo. The residue is slurried in heptane (1.5 L), filtered, washed with heptane (2×500 mL), and resulting solid. The solid is dried under vacuum to yield the title compound (450 g, 69% yield).

Step 4: Di-tert-butyl (1S,2R,3S,4R,5R,6R)-2-[(tert-butoxycarbonyl)amino]-3-[(3,4-dichlorobenzyl)oxy]-4-hydroxybicyclo[3.1.0]hexane-2,6-dicarboxylate

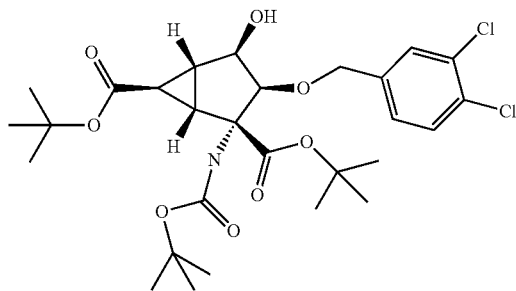 [SMILES: CC(C)(C)OC(=O)N[C@]1(C(=O)OC(C)(C)C)[C@@H]2[C@@H](C(=O)OC(C)(C)C)[C@@H]2[C@@H](O)[C@H]1OCc1ccc(Cl)c(Cl)c1]

To a solution of di-tert-butyl (1S,2R,3S,4R,5R,6R)-2-[(tert-butoxycarbonyl)amino]-3,4-dihydroxybicyclo[3.1.0] hexane-2,6-dicarboxylate (450 g, 1.05 mol) in dichloromethane (4.50 L) at room temperature is sequentially added 3,4-dichlorobenzyl bromide (144.73 mL, 238.80 g, 995.32 mmol), tetra-N-butylammonium chloride (58.24 g, 209.54 mmol), and a 50% wt/wt aqueous solution of sodium hydroxide (829.80 mL, 15.72 mol). After 7 hours, dilute the reaction with water (1 L) and separate the phases. Extract the organic phase with brine (500 mL), dry over anhydrous MgSO₄, filter and concentrate. Purify the residue by chromatography (2.5 kg of SiO₂; eluent: hexane/ethyl acetate 12:1 to 0:1) to give the title compound (539 g, 72% yield).

Step 5: Di-tert-butyl (1S,2R,3S,4S,5R,6R)-2-[(tert-butoxycarbonyl)amino]-3-[(3,4-dichlorobenzyl)oxy]-4-{[(4-nitrophenyl)carbonyl]oxy}bicyclo[3.1.0]hexane-2,6-dicarboxylate

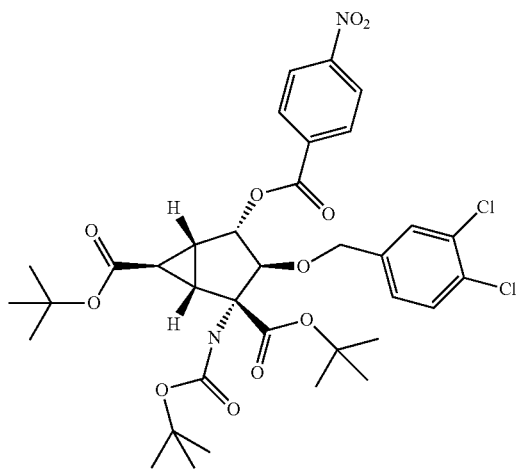 [SMILES: CC(C)(C)OC(=O)N[C@]1(C(=O)OC(C)(C)C)[C@@H]2[C@@H](C(=O)OC(C)(C)C)[C@@H]2[C@H](OC(=O)c2ccc([N+](=O)[O-])cc2)[C@H]1OCc1ccc(Cl)c(Cl)c1]

To a solution of di-tert-butyl (1S,2R,3S,4R,5R,6R)-2-[(tert-butoxycarbonyl)amino]-3-[(3,4-dichlorobenzyl)oxy]-4-hydroxybicyclo[3.1.0]hexane-2,6-dicarboxylate (539.00 g, 751.00 mmol) in tetrahydrofuran (6.76 L) is added triphenylphosphine (393.96 g, 1.50 mol) and 4-nitrobenzoic acid (251.02 g, 1.50 mol). The mixture is cooled to 10° C. whereupon diisopropyl azodicarboxylate (40% v/v in toluene, 744.41 mL, 759.30 g, 1.50 mol) is added dropwise over 15 minutes and allowed to warm to 23° C. After 18 hours, the mixture is diluted with methyl tert-butyl ether (2 L), washed sequentially with aq. sat. NaHCO₃ (2×2 L) and brine (1 L), and concentrated in vacuo. The residue is slurried in heptane (5 L) at 40° C. for 30 minutes then cooled to 23° C. The resulting solid is filtered and washed sequentially with heptane (2×500 mL), heptane/methyl tert-butyl ether (3×1 L). The combined filtrates are concentrated in vacuo and residue is purified by chromatography (2.5 kg of SiO₂; eluent:hexane/ethyl acetate 95:5 to 75:25) followed by recrystallization in heptane (10 L/kg) to yield the title compound as a white solid (273 g, 49% yield).

Step 6: Di-tert-butyl (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate

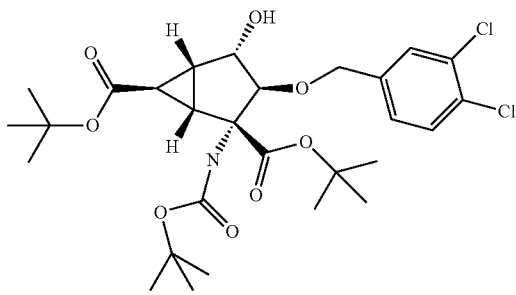 [SMILES: CC(C)(C)OC(=O)N[C@]1(C(=O)OC(C)(C)C)[C@@H]2[C@@H](C(=O)OC(C)(C)C)[C@@H]2[C@H](O)[C@H]1OCc1ccc(Cl)c(Cl)c1]

Potassium carbonate (153.45 g, 1.11 mol) is added to a suspension of di-tert-butyl (1S,2R,3S,4S,5R,6R)-2-[(tert-butoxycarbonyl)amino]-3-[(3,4-dichlorobenzyl)oxy]-4-{[(4-nitrophenyl)carbonyl]oxy}bicyclo[3.1.0]hexane-2,6-dicarboxylate (273.00 g, 370.11 mmol) in methanol (3.28 L) at ambient temperature. After 16 hours, the reaction is concentrated in vacuo. The residue is dissolved in methyl tert-butyl ether (2 L), and washed subsequently with water (0.8 L), brine (0.8 L), dried over MgSO₄, and concentrated in vacuo to yield the title compound as a white solid (215 g, 98% yield).

Step 7: (1S,2R,3S,4S,5R,6R)-2-Amino-3-[(3,4-dichlorobenzyl)oxy]-4-hydroxybicyclo[3.1.0]hexane-2,6-dicarboxylic acid hydrochloride

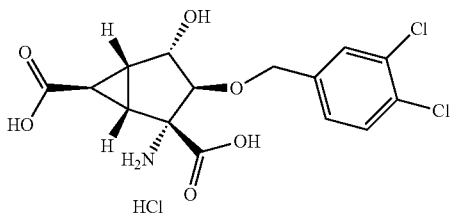 [SMILES: N[C@]1(C(=O)O)[C@@H]2[C@@H](C(=O)O)[C@@H]2[C@H](O)[C@H]1OCc1ccc(Cl)c(Cl)c1 ; Cl]

A mixture of water (430 mL) and 37% HCl in water (299.9 mL, 3.65 mol) is added to a suspension of di-tert-butyl (1S,2R,3S,4S,5R,6R)-2-[(tert-butoxycarbonyl)amino]-3-[(3,4-dichlorobenzyl)oxy]-4-hydroxybicyclo[3.1.0]hexane-2,6-dicarboxylate (215 g, 365.3 mmol) in 1,4-dioxane (73.1 mL). The resulting slurry is stirred at 100° C. for 4.5 hours, cooled to 25° C. and concentrated in vacuo to provide a white solid. Triturate sequentially with methyl tert-butyl ether (2 L) and hexanes (2 L) and then filter to collect the solids. Dry under vacuum for 16 hours. The solid is washed again with methyl tert-butyl ether (2×1 L) and hexane (1 L), then dried under vacuum at 50° C. overnight to yield the title compound as a white solid (140.4 g, 93% yield). MS (m/z): 376/378 (M+1).

Step 8: (1S,2R,3 S,4S,5R,6R)-2-[(tert-butoxycarbonyl)amino]-3-[(3,4-dichlorobenzyl)oxy]-4-hydroxybicyclo[3.1.0]hexane-2,6-dicarboxylic acid

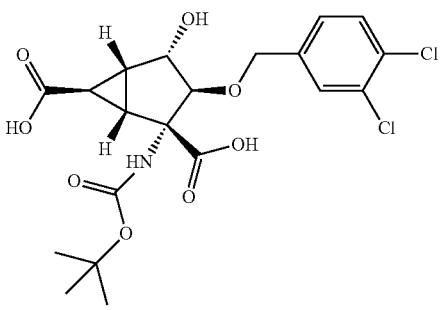 [SMILES: CC(C)(C)OC(=O)N[C@]1(C(=O)O)[C@@H]2[C@@H](C(=O)O)[C@@H]2[C@H](O)[C@H]1OCc1ccc(Cl)c(Cl)c1]

Triethylamine (212.80 mL, 154.49 g, 1.53 mol) and 2-(tert-butoxycarbonyloxyimino)-2-phenylacetonitrile (125.33 g, 508.90 mmol) are added sequentially to a suspension of (1S, 2R,3S,4S,5R,6R)-2-amino-3-[(3,4-dichlorobenzyl)oxy]-4-hydroxybicyclo[3.1.0]hexane-2,6-dicarboxylic acid hydrochloride (140 g, 339 mmol) in 1,4-dioxane (203.56 mL), and water (0.6 mL/mmol-pure-LR, 203.56 mL), at ambient temperature. After 4.5 hours, add additional 2-(tert-butoxycarbonyloxyimino)-2-phenylacetonitrile (25.07 g, 101.78 mmol) and triethylamine (23.64 mL, 17.17 g, 169.63 mmol) to the reaction and stir at 50° C. overnight. Cool to 23° C., dilute with water (500 mL), and wash with methyl tert-butyl ether (6×500 mL). Dilute the aqueous phase with 10% aq. HCl (300 mL; final pH=2) and extract with ethyl acetate (2×500 mL). The ethyl acetate extracts are dried over MgSO₄ and concentrated in vacuo to yield the title compound (148.3 g, 92% yield).

Step 9: Bis({[(1-methylethoxy)carbonyl]oxy}methyl)(1S,2R,3 S,4S,5R,6R)-2-[(tert-butoxycarbonyl)amino]-3-[(3,4-dichlorobenzyl)oxy]-4-hydroxybicyclo[3.1.0]hexane-2,6-dicarboxylate

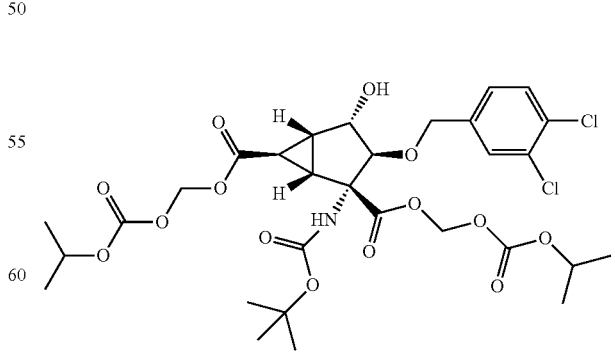

To a solution of bis({[(1-methylethoxy)carbonyl]oxy}methyl)(1S,2R,3S,4S,5R,6R)-2-[(tert-butoxycarbonyl)amino]-3-[(3,4-dichlorobenzyl)oxy]-4-hydroxybicyclo

[3.1.0]hexane-2,6-dicarboxylate (148.30 g, 311.35 mmol) in dimethylformamide (2.49 L) at 23° C. is sequentially added potassium carbonate (172.12 g, 1.25 mol), chloromethyl isopropyl carbonate (118.03 mL; 135.73 g, 871.79 mmol) and sodium iodide (9.33 g, 62.27 mmol). Stir for 18 hours. Dilute with methyl tert-butyl ether (2 L) and water (2 L). Separated the layers and wash the organic phase sequentially with water (200 mL) and brine (200 mL). Dry over anhydrous $MgSO_4$, filter and concentrate in vacuo. Purify the residue by chromatography (2.5 kg of $SiO_2$; eluent:hexane/ethyl acetate 3:1 to 1:1) to yield the title compound (167 g, 76% yield): MS (m/z): 608/610 (M−100 (—$CO_2$tBu)).

Step 10: Bis({[(1-methylethoxy)carbonyl]oxy}methyl)(1S,2R,3 S,4S,5R,6R)-2-[(tert-butoxycarbonyl)amino]-3-[(3,4-dichlorobenzyl)oxy]-4-hydroxybicyclo[3.1.0]hexane-2,6-dicarboxylate

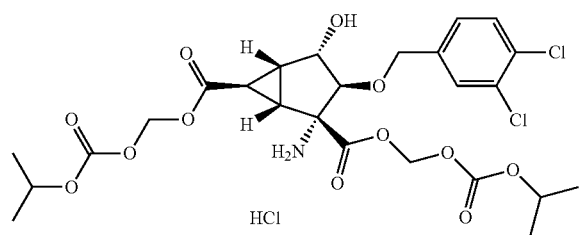 [SMILES: CC(C)OC(=O)OCOC(=O)[C@H]1[C@@H]2[C@H](O)[C@@H](OCc3ccc(Cl)c(Cl)c3)[C@@](N)(C(=O)OCOC(=O)OC(C)C)[C@H]12 ; Cl]

Bis({[(1-methylethoxy)carbonyl]oxy}methyl)(1S,2R,3 S,4S,5R,6R)-2-[(tert-butoxycarbonyl)amino]-3-[(3,4-dichlorobenzyl)oxy]-4-hydroxybicyclo[3.1.0]hexane-2,6-dicarboxylate (165.50 g, 233.58 mmol) is treated with 4M HCl in 1,4-dioxane (1.16 L, 4.63 mol) at 23° C. and stir for 2 hours. Volatiles are removed under vacuum. The residue obtained is slurried in methyl tert-butyl ether (1200 mL) overnight. The resulting solid is filtered, washed with methyl tert-butyl ether (2×100 mL), and dried under vacuum at 1 mbar/45° C. for 6 hours to yield the title compound as a white solid (134 g, 89% yield). MS (m/z): 608/610 (M+1)

Literature data (Witkin, Jeffrey M., and Eiler, William J. A. (2006), *Antagonism of Metabotropic Glutamate Group II Receptors in the Potential Treatment of Neurological and Neuropsychiatric Disorders*. Drug Development Research vol 67, pg. 757-769; and Yasuhara, Akito and Chaki, Shigeyuki, (2010) *Metabotropic Glutamate Receptors: Potential Drug Targets for Psychiatric Disorders*, The Open Medicinal Chemistry Journal, vol. 4, pg. 20-36.) and data generated in non-clinical animal studies support a role for mGlu2/3 antagonists in the treatment of depressive disorders and disorders of excessive sleepiness. Specifically, it is found that mGlu 2/3 receptor antagonists are effective in rodent models of depressive disorders and promote wakefulness using EEG monitored rodents without disproportionate or clinically relevant hyperactivity or overwhelming compensatory hypersomnolence. The increased alertness manifests in increased attention, improved cognitive performance, and a likelihood of reduced fatigue. As the previously described disorders represent common co-morbid clinical conditions, an mGlu2/3 receptor antagonist may be particularly effective in specific patient populations, such as patients with major depressive disorder, treatment refractory depression, unipolar depression, dysthymia, and/or cyclothimia, or any disorders of excessive sleepiness. Disorders of excessive sleepiness may include, but are not limited to excessive daytime sleepiness (EDS), hypersomnia associated with obstructive sleep apnea or narcolepsy, circadian rhythm sleep disorders (including, but not limited to shift work sleep disorder, jet lag disorder, delayed sleep phase disorder, advanced phase sleep disorder, and non-24 hour sleep-wake syndrome), idiopathic hypersomnolance and excessive sleepiness associated with non-restorative sleep (NRS)

To further demonstrate the characteristics of the present compounds, representative compounds may be run in the following in vitro and in vivo assays:

mGlu2 and mGlu3 Receptor cAMP Antagonist Assays

Antagonist activity is assayed in recombinant AV12 cells stably expressing human mGlu2 or mGlu3 receptors and the rat glutamate transporter EAAT1 (Excitatory Amino Acid Transporter 1). The cell lines are maintained by culturing in DMEM with high glucose and pyridoxine hydrochloride supplemented with 5% dialyzed fetal bovine serum (FBS), 1 mM sodium pyruvate, 1 mM HEPES and 1 mM L-glutamine; geneticin and hygromycin B are used as selection antibiotics. Confluent cultures are grown at 37° C. in an atmosphere containing 6.5% $CO_2$, and passaged biweekly. Cells are harvested using 0.25% trypsin, suspended in freeze media (FBS with 10% DMSO) at $10^7$ cells/ml, and aliquots are stored in liquid nitrogen. Twenty-four hours before the assay, cells are plated at a density of 8,000-10,000 cells per well in a tissue culture treated, 96-well, half-area black plates (Costar 3875) in 50 μl of DMEM with high glucose and pyridoxine hydrochloride supplemented with 5% dialyzed FBS, 1 mM sodium pyruvate, 1 mM HEPES, 100 μg/ml ampicillin, and 250 μM (mGlu2) or 125 μM (mGlu3) of L-glutamine.

Reversal of the inhibition of forskolin-stimulated cAMP production by test compounds is measured using homogeneous time resolved fluorescence technology (HTRF; Cisbio cat #62AM4PEB). The medium is removed and the cells are incubated with 100 μl cAMP stimulation buffer (STIM) for 30 minutes at 37° C. (STIM buffer contains 500 ml HBSS, 1000 ml DPBS, 0.034% BSA, 1.67 mM HEPES and 500 μM IBMX (Sigma 15879).) Compounds are tested in 10-point concentration response curves using 3× serial dilution followed by further 40-fold dilution into STIM buffer. DCG IV (Tocris 0975) serves as the reference agonist. The final reaction mixture contains 1 μM (for mGlu2) or 3 μM (for mGlu3) of forskolin (Sigma F6886), DCG IV at its $EC_{90}$, and up to 25 μM of test compound. Cells are incubated at 37° C. for 20 minutes. To measure the cAMP levels, cAMP-d2 conjugate and anti cAMP-cryptate conjugate in lysis buffer are incubated with the treated cells at room temperature for 1 hour (mGlu2) or 1.5 hour (mGlu3). The HTRF signal is detected using an EnVision plate reader (Perkin-Elmer) to calculate the ratio of fluorescence at 665 to 620 nM. The raw data are converted to cAMP amount (pmole/well) using a cAMP standard curve generated for each experiment. Relative $IC_{50}$ values are calculated from the top-bottom range of the concentration response curve using a four-parameter logistic curve fitting program (ActivityBase v5.3.1.22).

FLIPR and cAMP Assays for mGlu Receptor Selectivity

The relative antagonist potencies of the compounds of the invention for the other human mGlu receptors can be assessed with either a cAMP assay or fluorometric calcium response assay (see for example Fell et al., JPET (in press)). Briefly, individual AV12 cell lines containing the rat EAAT1 glutamate transporter and stably expressing the human mGlu1, 2, 3, 4, 5, 6, & 8 receptors are used for these studies. The mGlu1 and 5 receptors are Gi-coupled, so they naturally signal through phospholipase C, producing a calcium flux response which can be used to measure receptor activation using a Fluorometric Imaging Plate Reader (FLIPR, Molecular Devices). The cell lines expressing the mGlu2, 3, 4, and 8 receptor are designed to express the Gα15 subunit so that these Gi-coupled receptors will generate a calcium flux response similar to the mGlu1 and 5 receptor expressing cell lines. The mGlu6 receptor is tested in a cAMP format using methods analogous to those developed for mGlu2 and mGlu3 above. These cell lines are maintained as previously described except that amounts of L-glutamine and selection agents (geneticin, hygromycin B, zeocin, and blasticidin) may vary depending on the cell line. Confluent cultures are passaged biweekly.

Intracellular calcium levels are monitored using FLIPR before and after the addition of test compounds and Fluo-3 AM (Invitrogen) or Calcium 4 (Molecular Devices) dye, depending on the cell line. Cells are plated 24 hours prior to assay in a variable concentration of glutamine and a variable density of cells per well, depending on the cell line. The medium is removed and the cells are incubated with 8 µM of dye (50 µl per well) for 90 or 120 minutes (depending on cell line) at 25° C. A single-addition FLIPR assay generating an 11-point concentration response curve for the agonist glutamate is conducted prior to each experiment to confirm the appropriate sensitivity of the cells. The results are analyzed using GraphPad Prism v4.03 to calculate the concentrations of glutamate needed to induce the $EC_{90}$ (antagonist assay) and $EC_{10}$ (potentiator assay) responses.

Compounds are tested at each mGlu receptor in a two-addition FLIPR assay using a 10-point concentration response profile starting at a final concentration of 25 µM for the agonist assay and 12.5 µM for the potentiator and antagonist assays. The first addition detects any agonist activity, and the second addition consists of 100 µl of select concentrations (depending on cell line) of glutamate in assay buffer generating an $EC_{10}$ or $EC_{90}$ glutamate response. Agonist effects are quantified as percent stimulation induced by compound alone relative to the maximal glutamate response. Antagonist effects are quantified by calculating the percent inhibition of the $EC_{90}$ glutamate response caused by the compound. Potentiation effects are quantified as percent increase in the presence of an $EC_{10}$ response in glutamate relative to the $EC_{max}$ response. All data are calculated as relative $IC_{50}$ or $EC_{50}$ values using a four-parameter logistic curve fitting program (ActivityBase v5.3.1.22).

Antagonist activity in mGlu6 cells is measured using cAMP in a method analogous to that described above for mGlu2 and mGlu3 activity, except that the reference agonist was L-AP4 (Tocris). To measure mGlu6 agonist activity, the extent to which the compound inhibits the forskolin-stimulated cAMP production is calculated. Relative $IC_{50}$ and $EC_{50}$ values are calculated from the top-bottom range of the concentration response curve using a four-parameter logistic curve fitting program (ActivityBase v5.3.1.22).

Exemplified compounds wherein $R^1$ and $R^2$ are both hydrogen are tested essentially as described above and are found to have high antagonist potency for the mGlu2 and mGlu3 receptors. The exemplified compounds wherein $R^1$ and $R^2$ are both hydrogen are also found to be selective antagonists of the mGlu2 and mGlu3 receptors as against other mGlu receptor subtypes, having $IC_{50}$'s for the mGlu2 and mGlu3 receptors less than 70 nM and 50 nM, respectively, while the $IC_{50}$'s for other mGlu receptors tested are found to be significantly greater. See Table 1.

TABLE 1

Selectivity data

| Ex. | mGlu1 % inhib. @12.5 µM | mGlu2 IC50 nM | mGlu3 IC50 nM | mGlu4 % inhib. @12.5 µM | mGlu5 % inhib. @12.5 µM | mGlu6 IC50 nM | mGlu8 % inhib. @12.5 µM |
|---|---|---|---|---|---|---|---|
| 1 | −0.47% | 43.3 ± 5.8 | 27.2 ± 4.2 | 28.5% | 4.8% | 3300 | 78.4% ($IC_{50}$ 1900 nM) |
| 2 | 8.6% | 13.1 ± 1.9 | 7.8 | 69.0% | −12.9% | 1290 ± 162 | 92.3% ($IC_{50}$ 507 nM) |
| 3 | ND | 25.4 ± 4.8 | 10.8 | ND | ND | 2480 ± 295 | ND |
| 4 | −2% | 25.5 ± 2.8 | 8.2 ± 0.3 | 13.3% | 22.6% | 2640 ± 424 | 23.4% |
| 5 | ND | 16.8 ± 1.6 | 9.5 ± 4.6 | ND | ND | 1580 ± 141 | ND |
| 6 | ND | 18.6 ± 3.9 | 13.9 ± 2.4 | ND | ND | 1360 ± 433 | ND |
| 7 | 11.2% | 52 ± 17.9 | 34.8 ± 6.9 | 32.2% | 22.7% | 3690 | 46.7% |
| 8 | ND | 42.9 ± 1.8 | 26.0 ± 0.5 | ND | ND | 2580 | ND |
| 9 | 5% | 22 ± 3.0 | 4.4 ± 0.5 | 46.9% | 13.8% | 2820 | 13.3% |

ND = not determined

Further, certain compounds of the present invention show a lack of significant activity at other physiologically important receptors such as, but not limited to, the hERG channel, serotonin receptors (specifically $5\text{-}HT_{2A}$ and $5\text{-}HT_{2B}$), muscarinic receptors (specifically M2), and iGluR receptors (specifically iGluR5). The compound of example 1 is tested using known assay methods and is found to have no appreciable activity at these receptors.

Therefore, physiologically relevant doses of the compounds of the invention are expected to provide substantial inhibition of mGlu2 and mGlu3 receptors in vivo, while not substantially interacting with other mGlu receptors, or other physiologically relevant receptors, and thus are expected to provide the desired pharmacology while avoiding undesired effects associated with off-target activity.

Forced-Swim Test in Mice (mFST)

mFST is an established in vivo assay for antidepressant activity (Li et al. *J Pharmacol Exp Ther.* 319(1):254-9, 2006.). Mice treated with known clinically effective antidepressants (selective serotonin reuptake inhibitors and/or tricyclic antidepressants) exhibit the behavior of reduced time spent immobile after being placed in a water tank, a behavior associated with despair. The mFST was used to evaluate potential antidepressant-like activity of novel mGlu2/3 antagonists essentially as described in previously published methods (see for example, Li et al. *J Pharmacol Exp Ther.* 319(1):254-9, 2006.). Briefly, male NIH-Swiss mice (Harlan Sprague-Dawley, Indianapolis, Ind.) weighing between 25-30 g are used. Group housed animals are removed from the vivarium to the testing area in their own cages and allowed to adapt to the new environment for at least 1 hour before testing. Compounds where $R^1$ and $R^2$ are both hydrogen are dissolved in water with minimal NaOH added for dissolution and are administered i.p. Compounds where $R^1$ and/or $R^2$ are other than hydrogen are prepared on the day of use in 2.0-2.5% N-methyl-pyrrolidinone and then suspended in 1% HEC, 0.25% Tween 80, and 0.05% Dow antifoam, and administered orally. Mice are placed in a cylinder (diameter: 10 cm; height: 25 cm) filled with 6 cm of water (22-25° C.) for 6 min. The duration of immobility during the last 4 min. of the 6 min. period of the test was scored. A mouse is recorded as immobile when floating motionless or making only those movements necessary to keep its head above water.

Representative compounds are tested essentially as described above and are found to significantly reduce immobilization times in wild type mice. See Table 2. Therefore compounds of the present invention are expected to have antidepressant activity in vivo.

TABLE 2 mFST

| Example | $ED_{60}$ (mg/kg) | Maximal Decrease (1 − compound/control) * 100% |
|---|---|---|
| 1 | 1.0 (i.p.) | 59% |
| 2 | 2.08 (i.p.) | 62% |
| 3 | 8.2 (i.p.) | 47% |
| 4 | 9.5 (i.p.) | 38% |
| 5 | 7.45 (i.p.) | 56% |
| 6 | 7.3 (i.p.) | 47% |
| 7 | >10 (i.p.) | 18% |
| 8 | 9.1 (i.p.) | 41% |
| 9 | 9.68 (i.p.) | 41% |
| 10/15 | 22.1 (p.o.) | 50.5% |
| 11 | 51.5 (p.o.) | 32.9% |
| 12 | >28 (p.o.) | 7% |
| 13 | 11.3 (p.o.) | 62.8% |

In other experiments, mice with receptor deletions (mGlu2 knock-out mice) are studied; these mice are bred by heterozygote×heterozygote breeding and used as littermates for −/− and +/+ mouse comparisons (Taconic Farms). The compound of example 1 (10 mg/kg, i.p., 30 min prior) is found to significantly decrease immobility time in mGlu2+/+ mice, but not in mGlu2−/− mice. Similarly, the compound of example 10/15 (30 mg/kg, po, 120 min prior) is found to decrease immobility time in mGlu2+/+ mice, but not in mGlu2−/− mice. These findings further demonstrate that the mGlu2 receptor contributes to the antidepressant-like effects of the compounds of the invention.

The compounds of the invention may also be tested in combination with other compounds useful for the treatment of depressive disorders, as for example SSRI's, for their ability to enhance the antidepressant-like effects over that of either compound alone. The compound of example 10 (17 mg/kg p.o.) is tested in the mouse forced swim test alone and in combination with fluoxetine (10 mg/kg, i.p.) and found to significantly increase the antidepressant-like effect over that of either compound alone as shown in Table 3, below. Further, testing of brain and plasma levels of the active di-acid moiety of the compound of example 10 (i.e. the same compound as the freebase of example 1), show no increase in exposure levels, supporting the finding that the increased antidepressant-like activity was not due merely to an increase in central exposure to the compound.

TABLE 3 mFST with SSRI

| Compound(s) | Immobilization Time (sec.) | Std error of mean | Maximal Decrease (1 − compound/control) * 100% |
|---|---|---|---|
| Vehicle | 174 | 10 | |
| Example 10 | 105 | 12 | 24.5% |
| Fluoxetine | 161 | 8 | 7.6% |
| Ex. 10 + Fluoxetine | 66 | 19 | 62.1% |

Wakefulness and Behavioral Monitoring in Rats:

Representative compounds of the present invention are tested in rats for their ability to increase the amount of time in a state of wakefulness without undesired effects such as inhibition of REM sleep, waking motor impairment (disproportionate hyper- or hypolocomotion), and/or rebound hypersomnia Test animals are continuously monitored by electroencephalograms (EEG), electromyograms (EMG), and motion to measure cumulative time awake, rebound hypersomnia, and locomotor activity intensity during wakefulness. Methods for such studies are known in the art (see for example methods described in Edgar D M, Seidel W F. Modafinil induces wakefulness without intensifying motor activity or subsequent rebound hypersomnolence in the rat. *J Pharmacology & Experimental Therapeutics* 1997; 283: 757-769; van Gelder R N, Edgar D M, Dement W C. Real-time automated sleep scoring: validation of a microcomputer-based system for mice. Sleep 1991, 14: 48-55; and Gross B A, Walsh C M, Turakhia A A, Booth V, Mashour G A, Poe G R. Open-source logic-based automated sleep scoring software using electrophysiological recordings in rats. *J Neurosci Methods*. 2009; 184(1):10-8.) Studies are conducted as follows:

Animal Preparation.

Adult, male Wistar rats (approximately 270-300 g at time of surgery) are surgically fitted for chronic recording of EEG, EMG, body temperature, and motion as follows: Rats are surgically prepared with a cranial implant consisting of four stainless steel screws for EEG recording (two frontal [3.9 mm anterior from bregma, and ±2.0 mm mediolaterally] and two occipital [6.4 mm posterior from bregma, ±5.5 mm mediolaterally]), and with two Teflon-coated stainless steel wires for EMG recording (positioned under the nuchal trapezoid muscles). All leads are soldered to a miniature connector (Microtech, Boothwyn, Pa.) prior to surgery. The implant assembly is affixed to the skull by the combination of the stainless steel EEG recording screws, cyanoacrylate applied between the implant connector and skull, and dental acrylic. Body temperature and locomotor activity is monitored via a miniature transmitter (Minimitter PDT4000G, Philips Respironics, Bend, Oreg.) surgically placed into the abdomen. At least 3 weeks are allowed for recovery.

Recording Environment.

Each rat is housed individually within a microisolator cage modified with an inserted polycarbonate filter-top riser to allow more vertical headroom. A flexible cable that minimally restricts movement is connected at one end to a commutator affixed to the cage top and at the other end to the animal's cranial implant. Each cage is located within separate, ventilated compartments of a stainless steel sleep-wake recording chamber. Food and water are available ad libitum and the ambient temperature is maintained at about 23±1° C. A 24-hr light-dark cycle (LD 12:12) using fluorescent light is maintained throughout the study. Relative humidity averages approximately 50%. Animals are undisturbed for at least 30 hrs before and after each treatment.

Study Design and Dosing.

Compounds where $R^1$ and $R^2$ are both hydrogen are dissolved in water with minimal NaOH added for dissolution and are administered i.p in a volume of 1.0 mL per kg body weight. Compounds where $R^1$ and/or $R^2$ are other than hydrogen are administer p.o. in a volume of 2 mL per kg body weight in one of two alternative vehicles: i) 2.5% N-methyl-2-pyrrolidinone in hydroxyethylcellulose; or ii) 10% acacia with 0.05% Dow Corning® Antifoam in water. The vehicle or one of the compound dose levels is administered pseudo-randomly such that no rat receives the same treatment twice, and no rat receives more than two of the 8 treatments in any one study. Each rat is removed from its cage for about a minute to be weighed and treated. At least 6 days "washout" period precede and follow each treatment.

Data Collection.

Sleep and wakefulness discrimination may be automated (e.g., Van Gelder et al. 1991; Edgar et al. 1997, Winrow et al., 2010; Gross et al., 2009). EEG is amplified and filtered (X10,000, bandpass 1-30 Hz), EMG is amplified and integrated (bandpass 10-100 Hz, RMS integration), and non-specific locomotor activity (LMA) is monitored simultaneously. Arousal states are classified in 10 second epochs as non-REM sleep, REM sleep, wakefulness, or theta-dominated wakefulness. Locomotor activity (LMA) is recorded as counts per minute and is detected by commercially available telemetry receivers (ER4000, Minimitter, Bend, Oreg.).

Statistical Analysis.

Ages and body weights are summarized by mean, minimum and maximum over the treatment groups. All animals having at least one outcome are included in the summary results (for example, we include appropriate data from an animal treatment for which telemetry data are usable but EEG data are not). The post-treatment observation period is divided into 2 post-dosing intervals (the first 7 hours, and the first 19 hours) where the time of dosing is defined as the start of Hour=0. The outcomes are summarized in each period by computing either the mean hourly or the cumulative value across each period. Each outcome in each period is analyzed by analysis of covariance using treatment group and treatment date as factors and the corresponding pre-treatment interval, 24 hrs earlier, as the covariate. Adjusted means and the change from vehicle means and their corresponding standard errors are summarized for each treatment group. Adjusted Dunnett's multiple-comparison P-values are shown for each outcome in each period. Not all outcomes are analyzed in all periods, as shown in Table 1, which thus affect the experiment-wise type I error rate. As such, no further adjustments are made for multiple testing.

Determining Efficacy.

The threshold efficacious dose is estimated as the lowest dose for which cumulative time awake exceeds 50 minutes relative to vehicle controls across the first 7 hours post-treatment. A finer determination may be made by conducting subsequent studies of more closely spaced doses around the efficacious dose.

Determining Undesired Effects.

Two potentially undesired effects in particular are evaluated: rebound hypersomnolence and intensified motor activity (Edgar D M, Seidel W F, 1997).

(i) Rebound hypersomnolence may be measured as decreased levels of wakefulness during the period 8-19 hours after efficacious treatment doses. A biologically significant decrease is defined as a greater than 50 percent of the cumulative increase during the first 7 hours. Thus, if wakefulness increased by 100 minutes during the first 7 hours, then a decrease in cumulative wakefulness of 50 minutes or more, relative to vehicle controls, during the period 8-19 hours after treatment would be deemed biologically significant. Group mean changes, shown in Table 2, show a lack of rebound hypersomnolence.

(ii) Intensified motor activity is defined as an average increase relative to vehicle controls that exceeds 5 LMA counts per minute of EEG-defined wakefulness at the efficacy threshold dose, and for which the effect is dose related. Group mean increases in Table 2 were all under 5 counts per minute of wakefulness and are not dose dependent.

Exemplified compounds are tested essentially as described and are found to promote wakefulness without significant rebound hypersomnia or intensified motor activity. Exemplified compounds where $R^1$ and $R^2$ are both hydrogen (administered i.p.) are tested essentially as described and are found to be efficacious at doses of 10 mg/kg or lower. The compound of Example 10 is tested essentially as described and is found to have the cumulative time awake profile and locomotor activity intensity as shown in Table 4.

TABLE 4

| Dose (mg/kg PO) | N | Mean | SE | P |
|---|---|---|---|---|
| Cumulative Time Awake first 7 hours | | | | |
| 60 | 9 | 64.7 | 13.9 | <0.0001 |
| 30 | 8 | 48.8 | 14.4 | 0.0019 |
| 10 | 10 | 20.4 | 13.4 | 0.1387 |
| Cumulative Time Awake 8-19 hours | | | | |
| 60 | 9 | 34.7 | 12.4 | 0.0087 |
| 30 | 8 | 25.6 | 13.6 | 0.0696 |
| 10 | 10 | 15.2 | 12.3 | 0.2257 |
| Locomotor Activity Intensity(note 1) | | | | |
| 60 | 6 | 4.2 | 2.0 | 0.0427 |
| 30 | 5 | 0.5 | 2.1 | 0.8199 |
| 10 | 6 | 2.7 | 2.0 | 0.1999 |

Outcome statistics:
Mean values represent the difference from vehicle controls.
SE = standard error of the mean;
P = P-value adjusted for multiple contrasts for the efficacy variable. Unadjusted P values are shown for 'undesired effect' measures (Cumulative Time Awake 8-19 hours, and Locomotor Activity Intensity). Cumulative time awake given in minutes.
(note 1). Locomotor activity (LMA) intensity = counts of LMA per minute of EEG-defined wakefulness, averaged over the first 7 hr post-treatment.

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, subcutaneous, intravenous, and intramuscular. Such pharmaceutical compositions and processes for preparing them are well known in the art. See, e.g., Remington: The Science and Practice of Pharmacy (University of the Sciences in Philadelphia, ed., $21^{st}$ ed., Lippincott Williams & Wilkins Co., 2005). Compounds of Formula I where $R^1$ and/or $R^2$ are other than hydrogen are preferred for oral administration to improve bioavailability, whereas Compounds of Formula I where $R^1$ and $R^2$ are both hydrogen are preferred for i.v. or i.p. administration.

The compositions are preferably formulated in a unit dosage form, each dosage containing from about 1 to about 600 mg, more usually about 30 to about 300 mg, as for example between about 50 and about 250 mg of the active ingredient.

The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.01 to about 10 mg/kg, more usually from about 0.3 to 5.0 mg/kg, and as for example between 0.5 and 3.0 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula

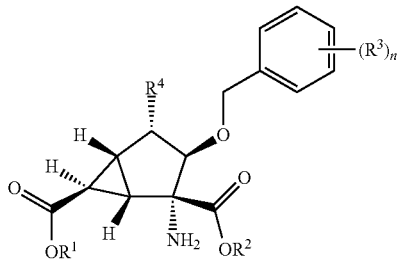

where $R^1$ and $R^2$ are each independently hydrogen, $C_1$-$C_3$ alkoxycarbonyloxymethyl, $C_1$-$C_3$ alkylcarbonyloxymethyl, or $C_{3-6}$ cycloalkylcarbonyloxymethyl;
$R^3$ is independently at each occurance methyl, fluoro, or chloro;
$R^4$ is hydroxyl, methylcarbonylamino, hydroxymethylcarbonylamino, methoxycarbonylamino, imidazol-2-ylsulfanyl, thiazol-2-ylsulfanyl, 1,2,4-triazolylsulfanyl, 1-methyl-1,2,4-triazol-3-ylsulfanyl, or 1-methyl-1,2,4-triazol-5-ylsulfanyl; and
n is 1 of 2;
or a pharmaceutically acceptable salt thereof.

2. The compound according to claim 1 where n is 2, both $R^3$ groups are chloro, and the chloro groups are at the phenyl 3- and 4-positions, or a pharmaceutically acceptable salt thereof.

3. The compound according to claim 1 where $R^1$ and $R^2$ are each hydrogen, or a pharmaceutically acceptable salt thereof.

4. The compound according to claim 1 where $R^1$ and $R^2$ are both other than hydrogen, or a pharmaceutically acceptable salt thereof.

5. The compound according to claim 1 where $R^1$ and $R^2$ are the same and are other than hydrogen, or a pharmaceutically acceptable salt thereof.

6. The compound according to claim 5 where $R^1$ and $R^2$ are each isopropyloxycarbonyloxymethyl.

7. The compound according to claim 1 which is (1S,2R,3S,4S,5R,6R)-2-amino-3-[(3,4-dichlorobenzyl)oxy]-4-hydroxybicyclo[3.1.0]hexane-2,6-dicarboxylic acid or a pharmaceutically acceptable salt thereof.

8. The compound according to claim 1 which is bis(isopropoxycarbonyloxymethyl) (1R,2S,3S,4R,5S,6R)-4-amino-3-[(3,4-dichlorophenyl)methoxy]-2-hydroxy-bicyclo[3.1.0]hexane-4,6-dicarboxylate or a pharmaceutically acceptable salt thereof.

9. A pharmaceutical composition comprising a compound of the formula

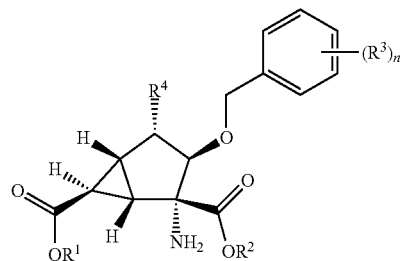

where $R^1$ and $R^2$ are each independently hydrogen, $C_1$-$C_3$ alkoxycarbonyloxymethyl, $C_1$-$C_3$ alkylcarbonyloxymethyl, or $C_{3-6}$ cycloalkylcarbonyloxymethyl;
$R^3$ is independently at each occurrence methyl, fluoro, or chloro;
$R^4$ is hydroxyl, methylcarbonylamino, hydroxymethylcarbonylamino, methoxycarbonylamino, imidazol-2-ylsulfanyl, thiazol-2-ylsulfanyl, 1,2,4-triazolylsulfanyl, 1-methyl-1,2,4-triazol-3-ylsulfanyl, or 1-methyl-1,2,4-triazol-5-ylsulfanyl; and
n is 1 of 2;
or a pharmaceutically acceptable salt thereof, and a pharmaceutically acceptable carrier, excipient or diluent.

10. A method for treating disorders of excessive sleepiness in a mammal comprising administering to a mammal in need of such treatment an effective amount of a compound according to claim 1, or a pharmaceutically acceptable salt thereof.

11. The method of claim 10 where the mammal is a human.

12. The pharmaceutical composition according to claim 9 wherein the compound is bis(isopropoxycarbonyloxymethyl) (1R,2S,3S,4R,5S,6R)-4-amino-3-[(3,4-dichlorophenyl)methoxy]-2-hydroxy-bicyclo[3.1.0]hexane-4,6-dicarboxylate or a pharmaceutically acceptable salt thereof.

* * * * *